United States Patent
Noshi et al.

(10) Patent No.: US 10,417,808 B2
(45) Date of Patent: Sep. 17, 2019

(54) IMAGE PROCESSING SYSTEM, IMAGE PROCESSING APPARATUS, AND IMAGE PROCESSING METHOD

(71) Applicant: Toshiba Medical Systems Corporation, Otawara-shi (JP)

(72) Inventors: Yasuhiro Noshi, Otawara (JP); Shinsuke Tsukagoshi, Nasushiobara (JP); Go Mukumoto, Utsunomiya (JP); Hiroyuki Onuki, Nasushiobara (JP); Shinya Kawanabe, Nasushiobara (JP); Atsushi Fukano, Otawara (JP); Tatsuya Watanabe, Nasushiobara (JP); Tomonori Ozaki, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 114 days.

(21) Appl. No.: 14/045,501

(22) Filed: Oct. 3, 2013

(65) Prior Publication Data

US 2014/0035914 A1    Feb. 6, 2014

Related U.S. Application Data

(63) Continuation of application No. PCT/JP2012/058936, filed on Apr. 2, 2012.

(30) Foreign Application Priority Data

Apr. 6, 2011 (JP) ................................. 2011-084800

(51) Int. Cl.
  *G06T 19/00*    (2011.01)
  *G06T 15/08*    (2011.01)
  (Continued)

(52) U.S. Cl.
  CPC ............ *G06T 15/08* (2013.01); *H04N 13/106* (2018.05); *H04N 13/30* (2018.05); *A61B 6/022* (2013.01);
  (Continued)

(58) Field of Classification Search
  CPC ....... G06T 19/00; G06T 15/08; G06T 7/0012; H04N 13/0239; H04N 13/0497; A61B 6/022; A61B 6/032
  (Continued)

(56) References Cited

U.S. PATENT DOCUMENTS

2005/0083246 A1    4/2005 Saishu et al.
2008/0055305 A1    3/2008 Blank et al.
(Continued)

FOREIGN PATENT DOCUMENTS

JP    07-182535 A    7/1995
JP    2000-268204 A    9/2000
(Continued)

OTHER PUBLICATIONS

International Search Report dated Jun. 19, 2012 in PCT/JP2012/058936 filed on Apr. 2, 2012.
(Continued)

*Primary Examiner* — Yi Yang
(74) *Attorney, Agent, or Firm* — Oblon, McClelland, Maier & Neustadt, L.L.P.

(57) ABSTRACT

An image processing system is provided, including an accepting unit, an acquisition unit, a measuring unit, and an output unit. The accepting unit accepts the setting of two coordinates in a stereoscopic image of a subject displayed on a stereoscopic image display device. The acquisition unit acquires volume data coordinates that are coordinates corresponding to stereoscopic image coordinates indicating the accepted coordinates. The measuring unit executes a mea-
(Continued)

suring process of measuring the distance between the two coordinates accepted by the accepting unit, based on the volume data coordinates acquired by the acquisition unit. The output unit outputs a result of measurement by the measuring unit.

10 Claims, 11 Drawing Sheets

(51) Int. Cl.
| | | |
|---|---|---|
| *H04N 13/30* | (2018.01) | |
| *H04N 13/106* | (2018.01) | |
| *A61B 6/00* | (2006.01) | |
| *A61B 8/00* | (2006.01) | |
| *A61B 8/08* | (2006.01) | |
| *H04N 13/00* | (2018.01) | |
| *A61B 6/02* | (2006.01) | |
| *A61B 6/03* | (2006.01) | |
| *H04N 13/341* | (2018.01) | |
| *H04N 13/305* | (2018.01) | |
| *H04N 13/275* | (2018.01) | |
| *H04N 13/351* | (2018.01) | |

(52) U.S. Cl.
CPC ............... *A61B 6/03* (2013.01); *A61B 6/466* (2013.01); *A61B 6/469* (2013.01); *A61B 6/5217* (2013.01); *A61B 6/5223* (2013.01); *A61B 8/466* (2013.01); *A61B 8/469* (2013.01); *A61B 8/483* (2013.01); *A61B 8/523* (2013.01); *A61B 8/5223* (2013.01); *H04N 13/275* (2018.05); *H04N 13/305* (2018.05); *H04N 13/341* (2018.05); *H04N 13/351* (2018.05); *H04N 2013/0081* (2013.01)

(58) Field of Classification Search
USPC ........... 345/419, 424; 348/42, 51; 378/41, 4; 382/128, 131
See application file for complete search history.

(56) References Cited

U.S. PATENT DOCUMENTS

| | | | |
|---|---|---|---|
| 2008/0292149 A1* | 11/2008 | Rasche .................... | 382/128 |
| 2009/0010519 A1* | 1/2009 | Wakai et al. ............ | 382/131 |
| 2010/0104150 A1* | 4/2010 | Saint Felix et al. ..... | 382/128 |
| 2011/0043615 A1* | 2/2011 | Saishu et al. ........... | 348/51 |
| 2011/0066031 A1* | 3/2011 | Lee ......................... | A61B 8/13 600/443 |
| 2012/0139911 A1 | 6/2012 | Saishu et al. | |

FOREIGN PATENT DOCUMENTS

| | | |
|---|---|---|
| JP | 2001-101451 A | 4/2001 |
| JP | 2001-149366 A | 6/2001 |
| JP | 2002-183759 A | 6/2002 |
| JP | 2004-187743 A | 7/2004 |
| JP | 2005-086414 A | 3/2005 |
| JP | 2009-028515 A | 2/2009 |

OTHER PUBLICATIONS

Office Action dated Jan. 5, 2016 in Japanese Patent Application No. 2011-084800.

\* cited by examiner

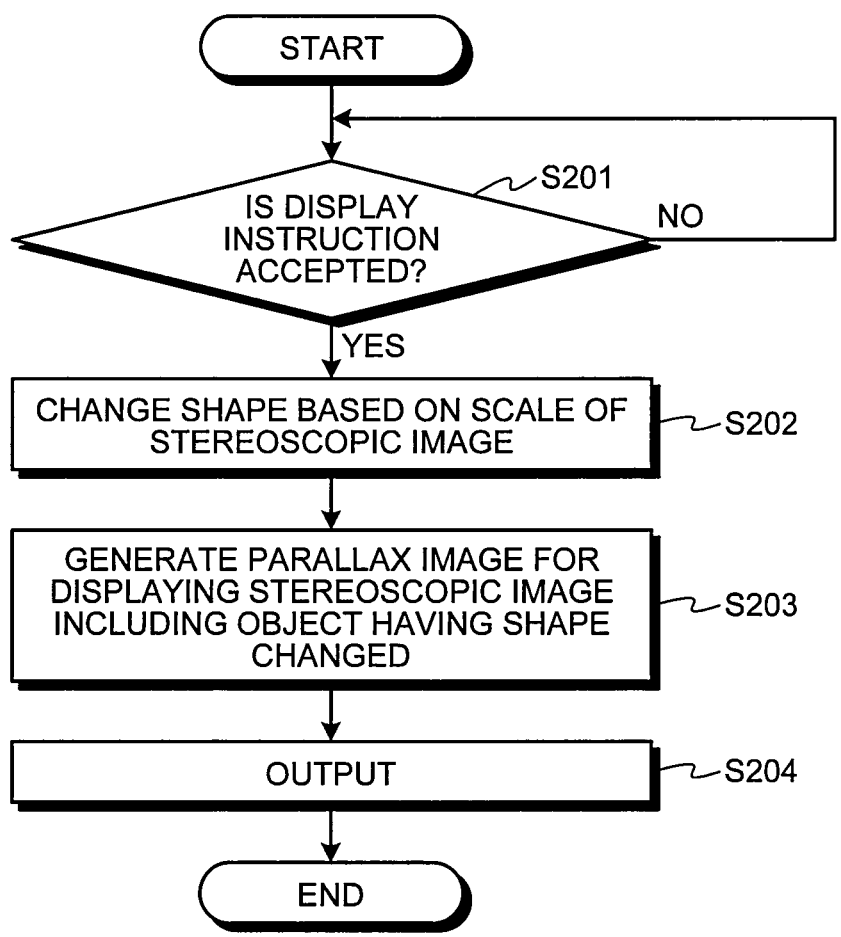

IMAGE PROCESSING SYSTEM, IMAGE PROCESSING APPARATUS, AND IMAGE PROCESSING METHOD

CROSS-REFERENCE TO RELATED APPLICATIONS

This application is a continuation of PCT international application Ser. No. PCT/JP2012/058936 filed on Apr. 2, 2012 which designates the United States, incorporated herein by reference, and which claims the benefit of priority from Japanese Patent Application No. 2011-084800, filed on Apr. 6, 2011, the entire contents of which are incorporated herein by reference.

FIELD

Embodiments described herein relate generally to an image processing system, an image processing apparatus, and an image processing method.

BACKGROUND

Conventionally, there exists a technique to display a stereoscopic image to a user using special equipment such as stereoscopic glasses by displaying two parallax images captured from two viewpoints on a monitor. In recent years, there also exists a technique to display a stereoscopic image to a user with the naked eyes by displaying multi-parallax images (for example, nine parallax images) captured from a plurality of viewpoints on a monitor using a light ray controller such as a lenticular lens.

Some medical image diagnosis apparatuses such as X-ray computed tomography (CT) devices, magnetic resonance imaging (MRI) devices, and ultrasonic diagnosis devices can generate three-dimensional medical images (hereinafter, volume data). Such a medical image diagnosis apparatus generates a planar image for display by executing a variety of image processing on volume data, and displays the generated image on a general monitor. For example, the medical image diagnosis apparatus generates a planar image of any given cross section that reflects three-dimensional information of a subject by executing a volume rendering process on volume data, and displays the generated planar image on a general monitor.

BRIEF DESCRIPTION OF THE DRAWINGS

FIG. 14 is a flowchart illustrating an example of the flow of a process performed by the workstation according to the second embodiment;

DETAILED DESCRIPTION

According to an embodiment, an image processing system includes an accepting unit, an acquisition unit, a measuring unit and an output unit. The accepting unit configured to accept setting of two coordinates in a stereoscopic image of a subject displayed on a stereoscopic image display device. The acquisition unit configured to acquire volume data coordinates that are coordinates corresponding to stereoscopic image coordinates that are coordinates in the stereoscopic image for indicating the coordinates accepted by the accepting unit, the volume data coordinates being coordinates in volume data of the subject that is stored in a prescribed storage device. The measuring unit configured to execute a measuring process of measuring a distance between the two coordinates accepted by the accepting unit, based on the volume data coordinates acquired by the acquisition unit. The output unit configured to output a result of measurement by the measuring unit.

Embodiments of an image processing system, an image processing apparatus, and an image processing method will be described in detail below with reference to the accompanying drawings. In the following, an image processing system including a workstation having a function as an image processing apparatus will be described as an embodiment.

First Embodiment

Figure 1:
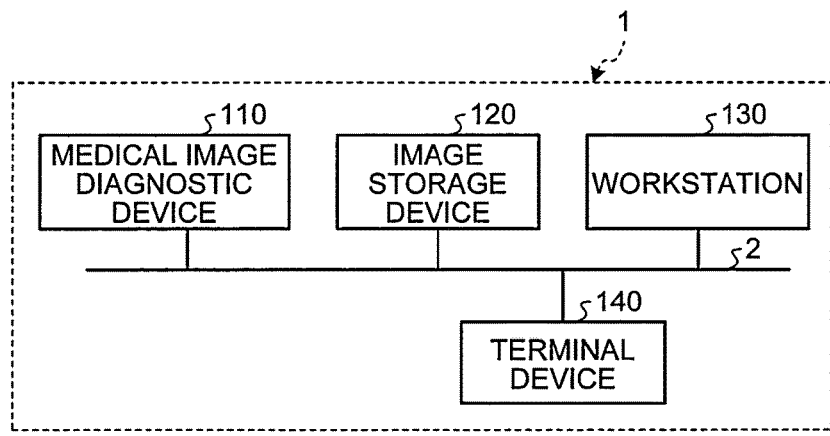
FIG. 1 is a diagram for explaining an exemplary configuration of an image processing system according to a first embodiment.

First of all, an exemplary configuration of an image processing system having an image processing apparatus according to a first embodiment will be described. FIG. 1 is a diagram for explaining an exemplary configuration of the image processing system according to the first embodiment.

As illustrated in FIG. 1, an image processing system 1 in the first embodiment has a medical image diagnosis device 110, an image storage device 120, a workstation 130, and a terminal device 140. The devices illustrated in FIG. 1 can directly or indirectly communicate with each other, for example, via an in-hospital local area network (LAN) 2 installed in a hospital. For example, in a case where the image processing system 1 has the picture archiving and communication system (PACS), the devices transmit/receive medical images and the like to/from each other in accordance with the digital imaging and communications in medicine (DICOM) standard.

The image processing system 1 provides a stereoscopic image to doctors and laboratory technicians working in a hospital by generating parallax images for displaying a stereoscopic image based on volume data generated by the medical image diagnosis device 110, and displaying the generated parallax images on a monitor capable of displaying a stereoscopic image.

Here, a "stereoscopic image" is displayed to a user by displaying a plurality of parallax images having different parallax angles that are captured from a plurality of viewpoints. In other words, "parallax images" are images having different parallax angles that are captured from a plurality of viewpoints for displaying a stereoscopic image to a user. Parallax images for displaying a stereoscopic image are generated, for example, by performing a volume rendering process on volume data.

The "parallax images" are individual images that constitute a "stereo vision image." In other words, the "stereo vision image" is constituted of a plurality of "parallax images" having different "parallax angles." A "parallax number" refers to the number of "parallax images" required to be stereoscopically viewed on a stereoscopic display monitor. The "parallax angle" refers to an angle determined by the position of volume data and the distance between viewpoint positions set to generate a "stereo vision image." "Nine-parallax images" described below indicates a "stereo vision image" constituted of nine "parallax images." "Two-parallax images" described below indicates a "stereo vision image" constituted of two "parallax images." A "stereoscopic image" is displayed to a user by displaying a stereo vision image, that is, by displaying a plurality of parallax images.

As described in detail below, in the first embodiment, the workstation 130 performs a variety of image processing on volume data and generates parallax images for displaying a stereoscopic image. The workstation 130 and the terminal device 140 each have a monitor capable of displaying a stereoscopic image and display a stereoscopic image to a user by displaying parallax images generated by the workstation 130 on the monitor. The image storage device 120 stores therein volume data generated by the medical image diagnosis device 110 and parallax images generated by the workstation 130. For example, the workstation 130 and the terminal device 140 acquire volume data or parallax images from the image storage device 120 and execute given image processing on the acquired volume data or parallax images, or display the parallax images on the monitor.

The medical image diagnosis device 110 is an X-ray diagnosis device, an X-ray computed tomography (CT) device, a magnetic resonance imaging (MRI) device, a ultrasonic diagnosis device, a single photon emission computed tomography (SPECT) device, a positron emission tomography (PET) device, a SPECT-CT device, which is a combination of a SPECT device and an X-ray CT device, a PET-CT device, which is a combination of a PET device and an X-ray CT device, or a group of these devices. The medical image diagnosis device 110 generates volume data.

Specifically, the medical image diagnosis device 110 in the first embodiment generates volume data by capturing an image of a subject. For example, the medical image diagnosis device 110 collects data such as projection data and an MR signal by capturing an image of a subject. Then, the medical image diagnosis device 110 generates volume data by reconstructing medical images of a plurality of axial planes that are along the body axis direction of the subject based on the collected data. For example, a description will be given using a case where the medical image diagnosis device 110 reconstructs 500 medical images of axial planes. In this case, a group of 500 medical images of axial planes that are reconstructed by the medical image diagnosis device 110 forms volume data. Projection data or an MR signal per se, for example, of the subject captured by the medical image diagnosis device 110 may be volume data.

The medical image diagnosis device 110 transmits volume data to the image storage device 120. When transmitting volume data to the image storage device 120, the medical image diagnosis device 110 transmits, as supplementary information, for example, a patient ID for identifying a patient, a test ID for identifying a test, a device ID for identifying the medical image diagnosis device 110, and a series ID for identifying one shot taken by the medical image diagnosis device 110.

The image storage device 120 is a database for storing therein medical images. Specifically, the image storage device 120 receives volume data from the medical image diagnosis device 110 and stores the received volume data in a prescribed memory. The image storage device 120 also receives a parallax image generated from volume data by the workstation 130 and stores the received parallax image in a prescribed memory. The image storage device 120 and the workstation 130 may be integrated together into one device.

In the first embodiment, the volume data or parallax image stored in the image storage device 120 is associated with a patient ID, a test ID, a device ID, a series ID, and the like for storage. Therefore, the workstation 130 and the terminal device 140 conduct a search using a patient ID, a test ID, a device ID, a series ID, and the like to acquire necessary volume data or parallax images from the image storage device 120.

The workstation 130 is an image processing apparatus to perform image processing on a medical image. Specifically, the workstation 130 acquires volume data from the image storage device 120. Then, the workstation 130 performs a variety of rendering processes on the acquired volume data to generate parallax images for displaying a stereoscopic image. For example, in a case where a stereoscopic image having two parallaxes is displayed to a user, the workstation 130 generates two parallax images having different parallax angles. For example, in a case where a stereoscopic image having nine parallaxes is displayed to a user, the workstation 130 generates nine parallax images having different parallax angles.

The workstation 130 has a monitor that can display a stereoscopic image (also called a stereoscopic display monitor or a stereoscopic image display device), as a display. The workstation 130 generates parallax images and displays the generated parallax images on the stereoscopic display monitor, thereby displaying a stereoscopic image to a user. As a result, the user of the workstation 130 can perform an operation for generating parallax images while viewing the stereoscopic image appearing on the stereoscopic display monitor.

The workstation 130 transmits the generated parallax image to the image storage device 120 or the terminal device 140. When transmitting the parallax image to the image storage device 120 or the terminal device 140, the workstation 130 transmits, for example, a patient ID, a test ID, a device ID, a series ID together as supplementary information. When doing so, the workstation 130 may transmit supplementary information such as the number of parallax images and the resolution together, considering that the resolution varies with monitors. The resolution is, for example, "466 pixels×350 pixels."

Here, the workstation 130 in the first embodiment accepts the setting of two coordinates in a stereoscopic image of a subject displayed on the stereoscopic image display device, as described in detail below. Then, the workstation 130 acquires volume data coordinates that correspond to stereoscopic image coordinates that are coordinates in a stereoscopic image for indicating the accepted coordinates, and that are coordinates in volume data of a subject stored in the image storage device 120. Then, the workstation 130 executes a measuring process of measuring the distance between the accepted two coordinates, based on the acquired volume data coordinates, and outputs the measurement result. As a result, according to the first embodiment, the measuring process of measuring the distance between two coordinates set to a stereoscopic image can be executed accurately.

Returning to explanation of FIG. 1, the terminal device 140 is a terminal that allows doctors and laboratory technicians working in a hospital to view a medical image. Specifically, the terminal device 140 has a stereoscopic display monitor as a display. The terminal device 140 acquires parallax images from the image storage device 120 and displays the acquired parallax images on the stereoscopic display monitor to display a stereoscopic image to the user. For example, when the terminal device 140 receives parallax images from the workstation 130, the terminal device 140 displays the received parallax images on the stereoscopic display monitor to display a stereoscopic image to the user. As a result, the users, namely, doctors and laboratory technicians can view a medical image that can be stereoscopically viewed. Examples of the terminal device 140 include a general-purpose personal computer (PC), a tablet terminal, and a mobile phone each having a stereoscopic display monitor. Another example of the terminal device 140 is any information processing terminal that is connected to a stereoscopic display monitor as an external device.

Here, the stereoscopic display monitor of the workstation 130 or the terminal device 140 will be described. An example of the stereoscopic display monitor displays two parallax images to display a stereoscopic image having two parallaxes (binocular parallax image) to a user who wears special equipment such as stereoscopic glasses.

Figure 2A:
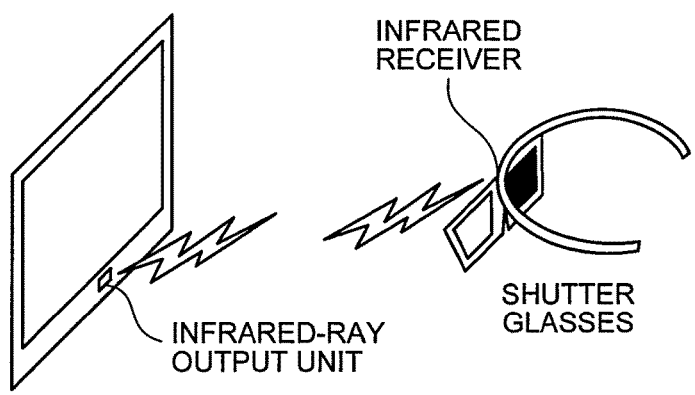
FIG. 2A is a diagram for explaining an example of a stereoscopic display monitor for stereoscopic display using two-parallax images.
Figure 2B:
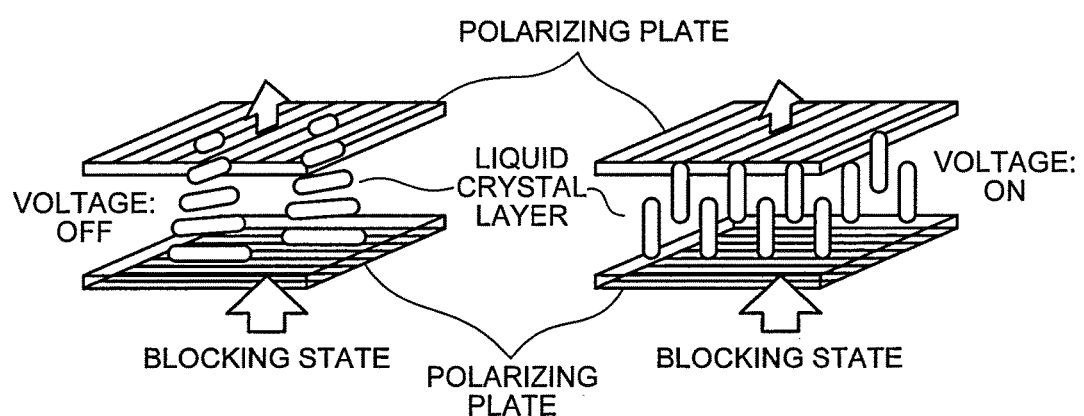
FIG. 2B is a diagram for explaining an example of a stereoscopic display monitor for stereoscopic display using two-parallax images.

FIG. 2A and FIG. 2B are diagrams for explaining an example of the stereoscopic display monitor for stereoscopic display using two-parallax images. In the example illustrated in FIG. 2A and FIG. 2B, a stereoscopic display monitor that performs stereoscopic display using a shutter system is illustrated. In the example illustrated in FIG. 2A and FIG. 2B, the user who observes the monitor wears shutter glasses as stereoscopic glasses. In the example illustrated in FIG. 2A and FIG. 2B, the stereoscopic display monitor alternately emits two parallax images. For example, the stereoscopic display monitor illustrated in FIG. 2A alternately emits a parallax image for the left eye and a parallax image for the right eye at 120 Hz. The stereoscopic display monitor has an infrared emitter, as illustrated in FIG. 2A. The infrared emitter controls infrared emission in accordance with a timing when parallax images are switched.

As illustrated in FIG. 2A, an infrared receiver of the shutter glasses receives infrared radiation emitted from the infrared emitter. Shutters are installed in left and right frames of the shutter glasses. The shutter glasses alternately switch a transmitting state and a blocking state of each of the left and right shutters in accordance with a timing when the infrared receiver receives infrared radiation.

Here, a process of switching the transmitting state and the blocking state in the shutters of the shutter glasses will now be described. As illustrated in FIG. 2B, each of the shutters has an entrance-side polarizing plate and an exit-side polarizing plate and additionally has a liquid crystal layer between the entrance-side polarizing plate and the exit-side polarizing plate. The entrance-side polarizing plate and the exit-side polarizing plate are orthogonal to each other as illustrated in FIG. 2B. Here, as illustrated in FIG. 2B, in the "OFF" state in which no voltage is applied, light having passed through the entrance-side polarizing plate is rotated by 90 degrees by the action of the liquid crystal layer and is allowed to pass through the exit-side polarizing plate. In short, the shutter to which no voltage is applied is in the transmitting state.

By contrast, as illustrated in FIG. 2B, in the "ON" state in which voltage is applied, the polarization-rotation action by liquid crystal molecules in the liquid crystal layer disappears, so that light having passed through the entrance-side polarizing plate is blocked by the exit-side polarizing plate. In short, the shutter to which voltage is applied is in the blocking state.

Based on this, the infrared emitter of the stereoscopic display monitor emits infrared radiation, for example, for a period during which an image for the left eye is displayed on the monitor. Then, the infrared receiver of the shutter glasses does not apply voltage to the shutter for the left eye and applies voltage to the shutter for the right eye for a period during which it is receiving the infrared radiation. Accordingly, as illustrated in FIG. 2A, the shutter for the right eye comes into the blocking state and the shutter for the left eye comes into the transmitting state. As a result, the image for the left eye enters only the user's left eye. By contrast, the infrared emitter of the stereoscopic display monitor stops infrared emission, for example, for a period during which an image for the right eye is displayed on the monitor. Then, the infrared receiver of the shutter glasses does not apply voltage to the shutter for the right eye and applies voltage to the shutter for the left eye for a period during which it is receiving no infrared radiation. Accordingly, the shutter for the left eye comes into the blocking state and the shutter for the right eye comes into the transmitting state. As a result, an image for the right eye enters only the user's right eye. In this manner, the stereoscopic display monitor illustrated in FIG. 2A displays a stereoscopic image to the user by switching the states of the shutters in accordance with the images displayed on the monitor.

Another example of the stereoscopic display monitor displays a stereoscopic image having nine parallaxes to the user with the naked eyes by using a light ray controller such as a lenticular lens. In this case, the stereoscopic display monitor enables a stereoscopic vision with binocular parallax and can display a stereoscopic image having motion parallax in which an image observed by the user changes with movement of the user's viewpoint.

Figure 3:
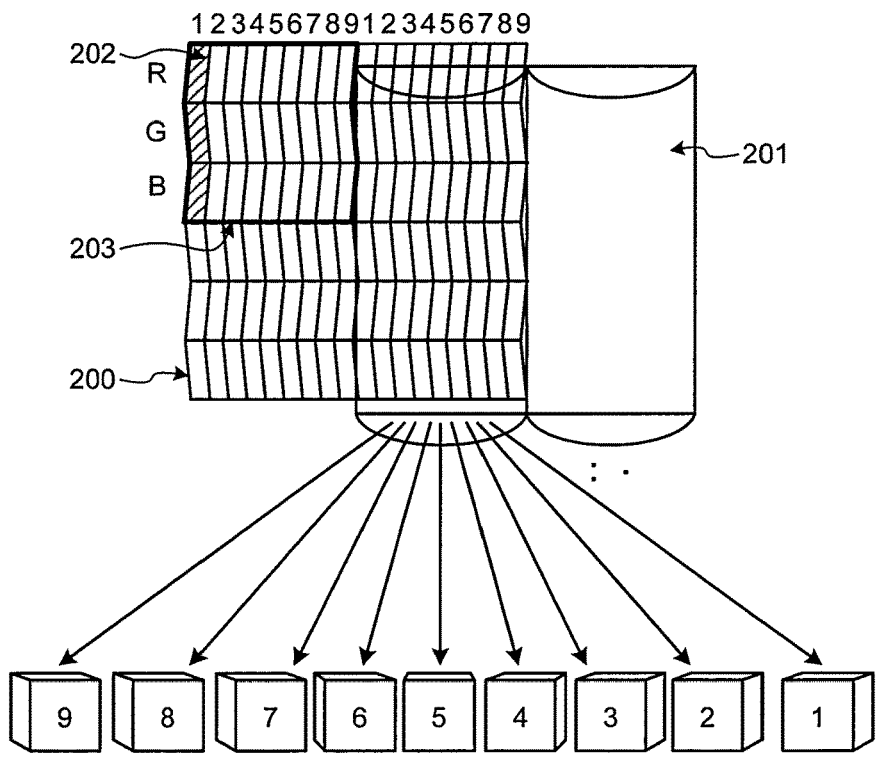
FIG. 3 is a diagram for explaining an example of a stereoscopic display monitor for stereoscopic display using nine-parallax images.

FIG. 3 is a diagram for explaining an example of the stereoscopic display monitor for stereoscopic display using nine-parallax images. The stereoscopic display monitor illustrated in FIG. 3 has a light ray controller arranged on the front surface of a flat display surface 200 such as a liquid crystal display panel. For example, in the stereoscopic display monitor illustrated in FIG. 3, a vertical lenticular sheet 201 having an optical aperture extending in the vertical direction is affixed to the front surface of the display surface 200. In the example illustrated in FIG. 3, the vertical lenticular sheet 201 is affixed such that a convex portion thereof faces forward. However, the vertical lenticular sheet 201 may be affixed such that the convex portion thereof faces the display surface 200.

In the example illustrated in FIG. 3, the display surface 200 has an aspect ratio of 3:1, in which pixels 202, each having three sub-pixels of red (R), green (G), and blue (B) arranged in the vertical direction, are arranged in a matrix pattern. In the example illustrated in FIG. 3, the stereoscopic display monitor outputs nine parallax images with different parallax angles that are arranged in a prescribed format (for example, a grid pattern), to the display surface 200. More specifically, the stereoscopic display monitor illustrated in FIG. 3 displays an intermediate image in which nine pixels at the same position in nine parallax images having different parallax angles are allotted to the respective nine rows of pixels 202. The nine rows of pixels 202 form a unit pixel group 203 that simultaneously displays nine images having different parallax angles. In the example illustrated in FIG. 3, the intermediate image is formed in a grid pattern. However, the intermediate image is not limited thereto and may be formed in any shape.

Nine parallax images having different parallax angles, which are simultaneously output as the unit pixel group 203 on the display surface 200, are radiated as parallel light beams, for example, by a light emitting diode (LED) backlight and further radiated by the vertical lenticular sheet 201 in multiple directions. Light from pixels of the nine parallax images are radiated in multiple directions, whereby light entering the user's right and left eyes change in accordance with the position of the user (position of viewpoint). In other words, the parallax image entering the right eye and the parallax image entering the left eye are parallax images having different angles of view depending on the angle from which the user views. As a result, the user can visually recognize a stereoscopic image, in which the user views a target from different parallax angles at the nine positions illustrated in FIG. 3, for example. For example, the user can stereoscopically recognize a target while facing the target straightforwardly at the position "5" illustrated in FIG. 3, and can also stereoscopically recognize the target with its orientation changed at the positions other than "5" illustrated in FIG. 3. The example in FIG. 3 is illustrated only by way of example, and embodiments are not limited thereto. For example, in the example illustrated in FIG. 3, a combination of a horizontal stripe (RRR . . . , GGG . . . , BBB . . . ) liquid crystal and a vertical lens is used. However, embodiments are not limited thereto, and a combination of a vertical stripe (RGBRGB . . . ) liquid crystal and an oblique lens may be used, for example.

An exemplary configuration of the image processing system 1 in the first embodiment has been described briefly so far. Application of the image processing system 1 as described above is not limited to the case where PACS has been introduced. For example, the image processing system 1 may be applied similarly to a case where an electronic medical record system for managing electronic medical records with medical images has been introduced. In this case, the image storage device 120 is a database that stores therein electronic medical records. For example, the image processing system 1 may also be applied similarly to a case where the Hospital Information System (HIS) or the Radiology Information System (RIS) has been introduced. The image processing system 1 is not limited to the exemplary configuration above. The function and functional distribution of each device may be changed as appropriate according to the manner of operation.

Figure 4:
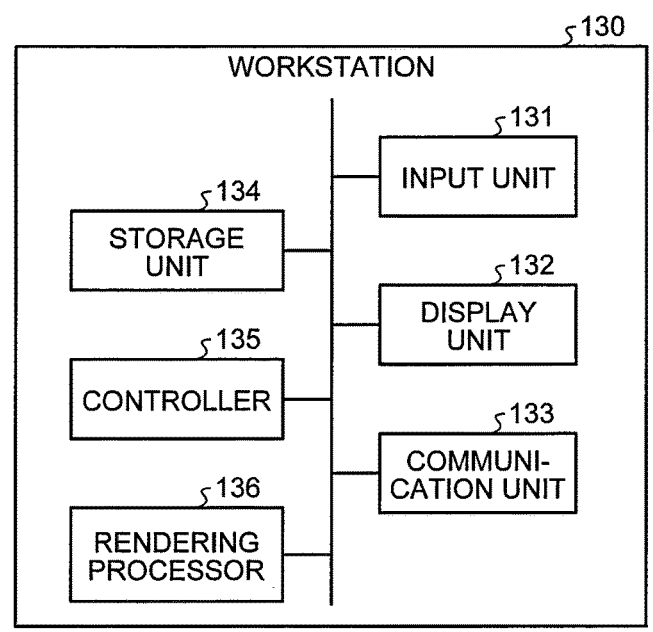
FIG. 4 is a diagram for explaining an exemplary configuration of a workstation according to the first embodiment.

An exemplary configuration of the workstation 130 in the first embodiment will now be described using FIG. 4. FIG. 4 is a diagram for explaining an exemplary configuration of the workstation according to the first embodiment.

The workstation 130 is a high-performance computer suitable for image processing, for example. In the example illustrated in FIG. 4, the workstation 130 includes an input unit 131, a display 132, a communication unit 133, a storage unit 134, a controller 135, and a rendering processor 136. In the following description, the workstation 130 is a high-performance computer suitable for image processing, for example. However, not being limited thereto, the workstation 130 may be any information processing apparatus. For example, the workstation 130 may be any personal computer.

The input unit 131 is, for example, a mouse, a keyboard, or a track ball for accepting the user's input of a variety of operations on the workstation 130. Specifically, the input unit 131 accepts input of information for acquiring volume data subjected to a rendering process from the image storage device 120. For example, the input unit 131 accepts input of a patient ID, a test ID, a device ID, and a series ID. The input unit 131 also accepts input of conditions concerning a rendering process (hereinafter, the rendering conditions).

The display 132 is a liquid crystal panel or the like as a stereoscopic display monitor for displaying various types of information. Specifically, the display 132 in the first embodiment displays a graphical user interface (GUI) for accepting a variety of operations from the user or a stereoscopic image, for example. The communication unit 133 is, for example, a network interface card (NIC) for communication with other devices. For example, the communication unit 133 receives from the terminal device 140 the rendering conditions input to the terminal device 140 by the user.

The storage unit 134 is, for example, a hard disk or a semiconductor memory device for storing therein various types of information. Specifically, the storage unit 134 stores therein volume data acquired from the image storage device 120 through the communication unit 133. The storage unit 134 also stores therein volume data during a rendering process, a parallax image subjected to a rendering process, and supplementary information thereof (e.g., parallax number, resolution), for example.

The controller 135 is, for example, an electronic circuit such as a central processing unit (CPU), a micro processing unit (MPU), or a graphics processing unit (GPU), or an integrated circuit such as an application specific integrated circuit (ASIC) or a field programmable gate array (FPGA) for controlling the workstation 130 on the whole.

For example, the controller 135 controls display of a GUI and display of a stereoscopic image on the display 132. For example, the controller 135 controls transmission/reception of volume data and parallax images to/from the image storage device 120 through the communication unit 133. For example, the controller 135 controls a rendering process performed by the rendering processor 136. For example, the controller 135 controls read of volume data from the storage unit 134 and storage of a parallax image in the storage unit 134.

Here, the controller 135 of the workstation 130 controls a rendering process performed by the rendering processor 136 and cooperates with the rendering processor 136 to execute a measuring process. The details of the controller 135 will be described later after a description of the rendering processor 136.

The rendering processor 136 performs a variety of rendering processes on volume data acquired from the image storage device 120 and generates a parallax image, under control of the controller 135. Specifically, the rendering processor 136 reads volume data from the storage unit 134 and performs pre-processing on the read volume data. Then, the rendering processor 136 performs a volume rendering process on the volume data after the pre-processing to generate a parallax image for displaying a stereoscopic image. Then, the rendering processor 136 stores the generated parallax image in the storage unit 134.

The rendering processor 136 may generate an overlay image in which various types of information (e.g., scale, patient name, and test item) is represented, and may superimpose the generated overlay image on a parallax image. In this case, the rendering processor 136 stores the parallax image having the overlay image superimposed thereon in the storage unit 134.

A rendering process refers to image processing as a whole that is performed on volume data. A volume rendering process is one of rendering processes and refers to a process for generating a medical image reflecting three-dimensional information of a subject. The medical image generated by the rendering process is, for example, a parallax image.

Figure 5:
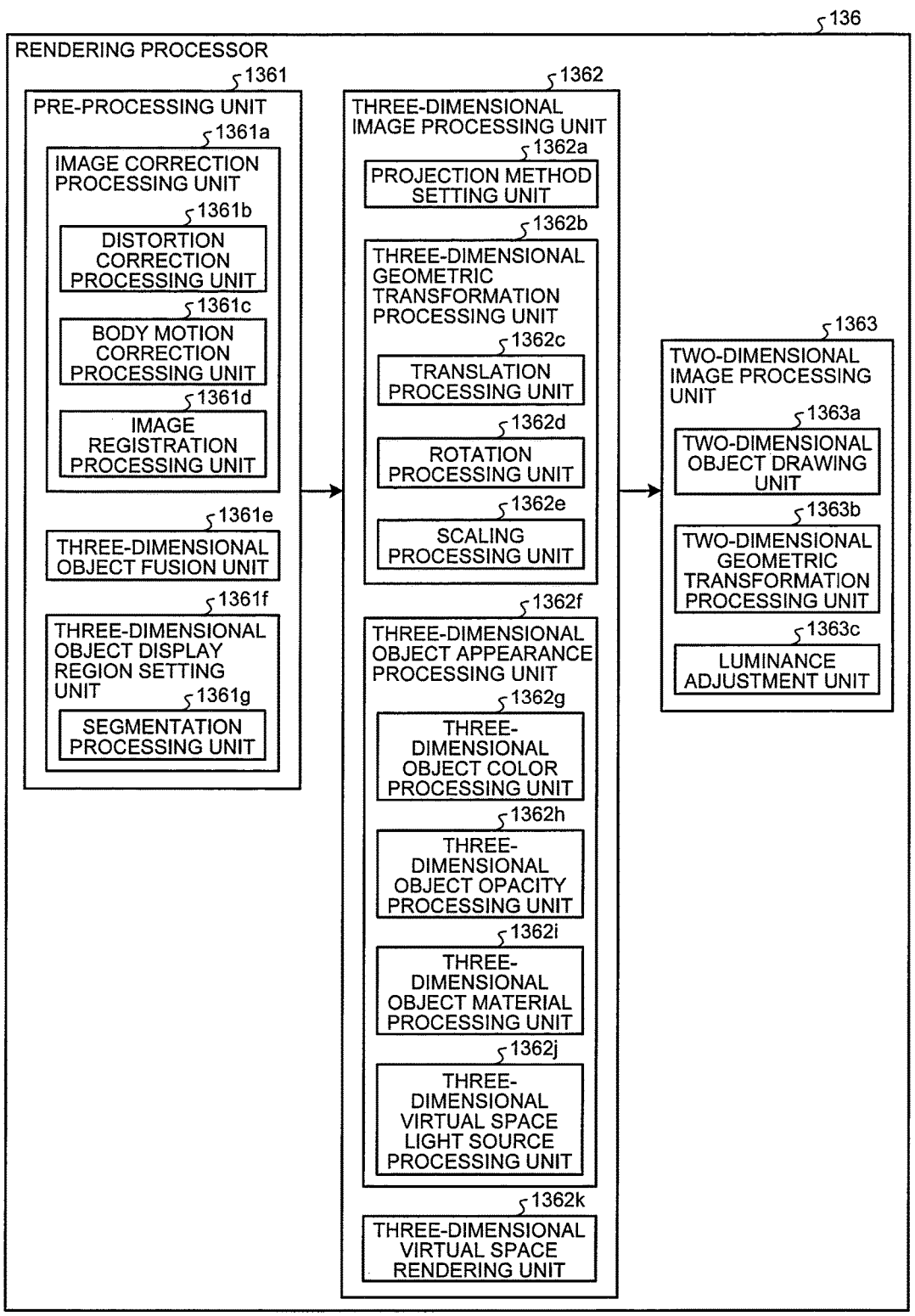
FIG. 5 is a diagram for explaining an exemplary configuration of a rendering processor illustrated in FIG. 4.

FIG. 5 is a diagram for explaining an exemplary configuration of the rendering processor illustrated in FIG. 4. As illustrated in FIG. 5, the rendering processor 136 includes a pre-processing unit 1361, a three-dimensional image processing unit 1362, and a two-dimensional image processing unit 1363. As described in detail below, the pre-processing unit 1361 performs pre-processing on volume data. The three-dimensional image processing unit 1362 generates a parallax image from the volume data after pre-processing. The two-dimensional image processing unit 1363 generates a parallax image having various types of information superimposed on a stereoscopic image.

The pre-processing unit 1361 performs a variety of pre-processing before a rendering process is performed on volume data. In the example illustrated in FIG. 5, the pre-processing unit 1361 includes an image correction processing unit 1361a, a three-dimensional object fusion unit 1361e, and a three-dimensional object display region setting unit 1361f.

The image correction processing unit 1361a performs an image correction process when two kinds of volume data are processed as one piece of volume data. In the example illustrated in FIG. 5, the image correction processing unit 1361a includes a distortion correction processing unit 1361b, a body motion correction processing unit 1361c, and an image registration processing unit 1361d. For example, the image correction processing unit 1361a performs an image correction process when volume data of a PET image and volume data of an X-ray CT image generated by a PET-CT device are processed as one piece of volume data. The image correction processing unit 1361a also performs an image correction process when volume data of a T1 weighted image and volume data of a T2 weighted image generated by an MRI device are processed as one piece of volume data.

Here, the distortion correction processing unit 1361b of the image correction processing unit 1361a corrects a distortion of data resulting from the collecting conditions during data collection by the medical image diagnosis device 110, in individual pieces of volume data. The body motion correction processing unit 1361c corrects a movement resulting from a body motion of a subject during collection of data used to generate individual pieces of volume data. The image registration processing unit 1361d performs registration using, for example, a cross-correlation method between two pieces of volume data subjected to the correction process performed by the distortion correction processing unit 1361b and the body motion correction processing unit 1361c.

The three-dimensional object fusion unit 1361e fuses a plurality of pieces of volume data registered by the image registration processing unit 1361d. The processing in the image correction processing unit 1361a and the three-dimensional object fusion unit 1361e is omitted when a rendering process is performed on a single piece of volume data.

The three-dimensional object display region setting unit 1361f sets a display region corresponding to a display target organ designated by the user. In the example illustrated in FIG. 5, the three-dimensional object display region setting unit 1361f includes a segmentation processing unit 1361g. The segmentation processing unit 1361g of the three-dimensional object display region setting unit 1361f extracts a user-designated organ such as heart, lung, or blood vessel, for example, by a region growing method based on a pixel value (voxel value) of volume data.

The segmentation processing unit 1361g does not perform a segmentation process if a display target organ is not designated by the user. When the user designates a plurality of display target organs, the segmentation processing unit 1361g extracts a plurality of corresponding organs. The processing in the segmentation processing unit 1361g may be executed again by a request for fine adjustment by the user who refers to the rendering image.

The three-dimensional image processing unit 1362 performs a volume rendering process on volume data after the pre-processing performed by the pre-processing unit 1361. In the example illustrated in FIG. 5, the three-dimensional image processing unit 1362 includes, as processing units for performing a volume rendering process, a projection method setting unit 1362a, a three-dimensional geometric transformation processing unit 1362b, a three-dimensional object appearance processing unit 1362f, and a three-dimensional virtual space rendering unit 1362k.

The projection method setting unit 1362a determines a projection method for generating a stereoscopic image. For example, the projection method setting unit 1362a determines whether a volume rendering process is executed by parallel projection or executed by perspective projection.

The three-dimensional geometric transformation processing unit 1362b determines information for three-dimensionally geometrically transforming volume data to be subjected to a volume rendering process. In the example illustrated in FIG. 5, the three-dimensional geometric transformation processing unit 1362b includes a translation processing unit 1362c, a rotation processing unit 1362d, and a scaling processing unit 1362e. The translation processing unit 1362c of the three-dimensional geometric transformation processing unit 1362b determines the amount of movement to translate volume data when a viewpoint position in a volume rendering process is translated. The rotation processing unit 1362d determines the amount of movement to rotate volume data when a viewpoint position in a volume rendering process is rotated. The scaling processing unit 1362e determines an enlargement ratio or a reduction ratio of volume data when a request for enlarging or reducing a stereoscopic image is made.

The three-dimensional object appearance processing unit 1362f includes a three-dimensional object color processing unit 1362g, a three-dimensional object opacity processing unit 1362h, a three-dimensional object material processing unit 1362i, and a three-dimensional virtual space light source processing unit 1362j. The three-dimensional object appearance processing unit 1362f determines a display state of a stereoscopic image displayed to the user by displaying parallax images with those processing units, in response to a request by the user, for example.

The three-dimensional object color processing unit 1362g determines a color to be applied to each segmented region of volume data. The three-dimensional object opacity processing unit 1362h is a processing unit that determines the opacity of each voxel that constitutes each segmented region of volume data. A region behind a region having opacity "100%" in volume data is not represented in a parallax image. A region having opacity "0%" in volume data is not represented in a parallax image.

The three-dimensional object material processing unit 1362i determines a material of each segmented region in volume data to adjust texture when this region is represented. The three-dimensional virtual space light source processing unit 1362j determines the position of a virtual light source placed in a three-dimensional virtual space and the kind of the virtual light source when a volume rendering process is performed on volume data. Examples of the kind of the virtual light source include a light source that radiates a parallel light beam from an infinite distance, and a light source that radiates a radiant light beam from a viewpoint.

The three-dimensional virtual space rendering unit 1362k performs a volume rendering process on volume data to generate a parallax image. The three-dimensional virtual space rendering unit 1362k uses a variety of information determined by the projection method setting unit 1362a, the three-dimensional geometric transformation processing unit 1362b, and the three-dimensional object appearance processing unit 1362f, as necessary, when performing a volume rendering process.

Here, the three-dimensional virtual space rendering unit 1362k accepts the rendering conditions from the controller 135 and performs a volume rendering process on volume data in accordance with the accepted rendering conditions. The rendering conditions are accepted from the user through the input unit 131, set by default, or accepted from the terminal device 140 through the communication unit 133. Here, the projection method setting unit 1362a, the three-dimensional geometric transformation processing unit 1362b, and the three-dimensional object appearance processing unit 1362f determine a variety of necessary information in accordance with the rendering conditions, so that the three-dimensional virtual space rendering unit 1362k generates a stereoscopic image using the information thus determined.

For example, the rendering condition is "parallel projection" or "perspective projection." For example, the rendering condition is "a reference viewpoint position and a parallax angle." For example, the rendering conditions are "translation of a viewpoint position," "rotation of a viewpoint position," "enlargement of a stereoscopic image," and "reduction of a stereoscopic image." For example, the rendering conditions are "a color to be applied," "transparency," "texture," "the position of a virtual light source," and "the kind of a virtual light source."

Figure 6:
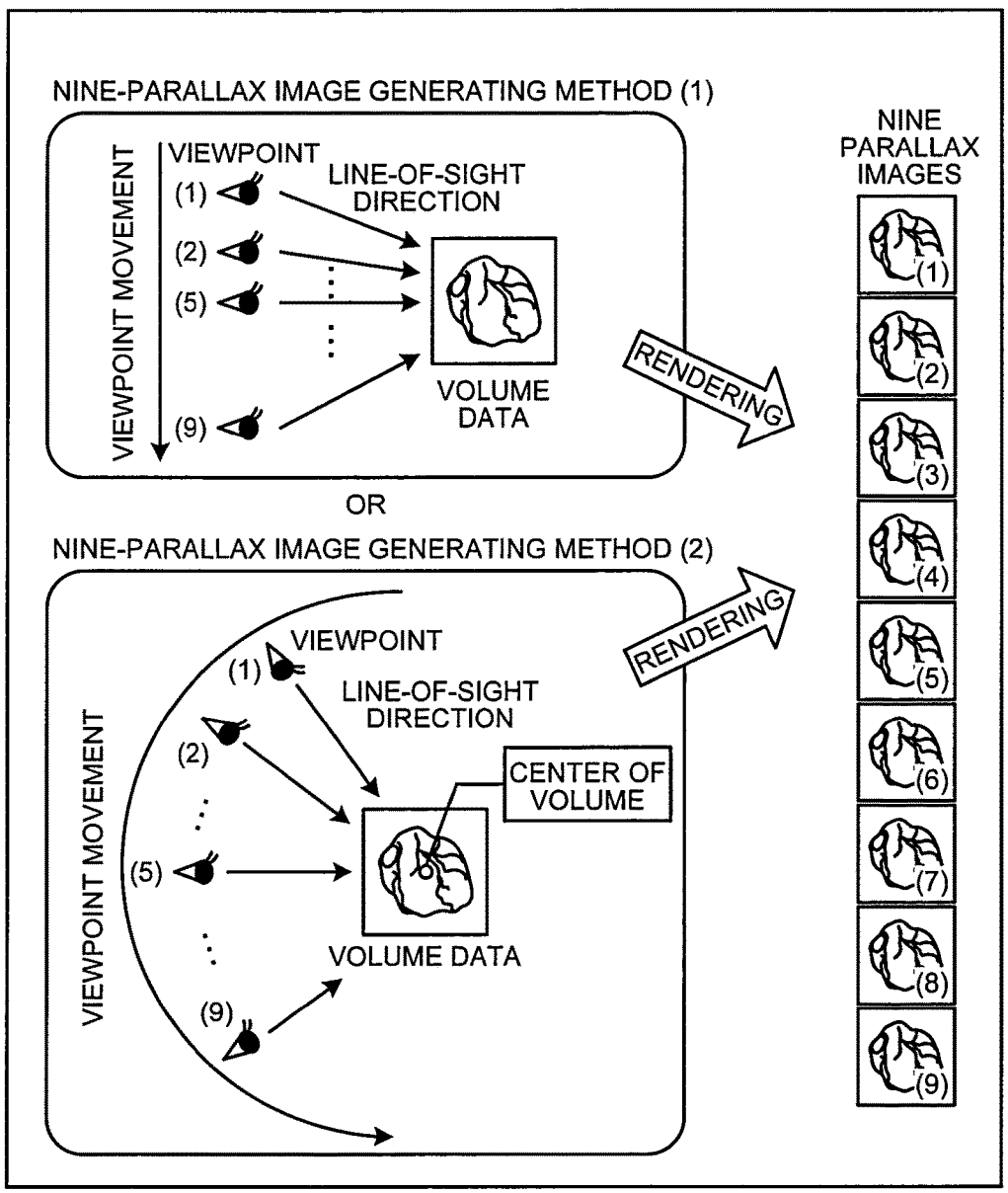
FIG. 6 is a diagram for explaining an example of a volume rendering process according to the first embodiment.

FIG. 6 is a diagram for explaining an example of the volume rendering process according to the first embodiment. For example, it is assumed that the three-dimensional virtual space rendering unit 1362k accepts parallel projection and further accepts a reference viewpoint position (5) and a parallax angle "1°" as rendering conditions, as illustrated in the "nine-parallax images generating method (1)" in FIG. 6. In this case, the three-dimensional virtual space rendering unit 1362k translates the positions of the viewpoints from (1) to (9) such that the parallax angles are at intervals of "1°," whereby nine parallax images having parallax angles (the angle between line of sight directions) different by 1° are generated by parallel projection. In the case where parallel projection is performed, the three-dimensional virtual space rendering unit 1362k sets a light source that radiates a parallel light beam from an infinite distance along a line of sight direction.

Alternatively, the three-dimensional virtual space rendering unit 1362k accepts perspective projection and further accepts a reference viewpoint position (5) and a parallax angle "1" as rendering conditions, as illustrated in the "nine-parallax images generating method (2)" in FIG. 6. In this case, the three-dimensional virtual space rendering unit 1362k rotates the positions of the viewpoints from (1) to (9) such that the parallax angles are at intervals of "1°" about the centroid of the cross-sectional plane of volume data that is present on the plane on which the viewpoint is moved, whereby nine parallax images having parallax angles different by 1° are generated by perspective projection. In other words, nine parallax images are generated through rotation not about the centroid of the three-dimensional volume but about the centroid of the two-dimensional cross-sectional plane. In the case where perspective projection is performed, the three-dimensional virtual space rendering unit 1362k sets a point light source or a surface light source that emits light three-dimensionally and radially around a line of sight direction, for each viewpoint. In the case where perspective projection is performed, depending on the rendering conditions, the viewpoints (1) to (9) may be translated.

The three-dimensional virtual space rendering unit 1362k may perform a volume rendering process by combining parallel projection with perspective projection by setting a light source that emits light two-dimensionally and radially around a line of sight direction for the vertical direction of the volume rendering image to be displayed and a light source that radiates a parallel light beam from an infinite distance along a line of sight direction for the horizontal direction of the volume rendering image to be displayed.

In the example in FIG. 6, a projection method, a reference viewpoint position, and a parallax angle are accepted as the rendering conditions. When any other conditions are accepted as the rendering conditions, the three-dimensional virtual space rendering unit 1362k generates nine parallax images that reflect the rendering conditions in a similar manner.

The three-dimensional virtual space rendering unit 1362k has a function of reconstructing a multi planar reconstruction (MPR) image from volume data by performing not only volume rendering but also MPR. In addition, the three-dimensional virtual space rendering unit 1362k has a function of performing "Curved MPR" as MPR and a function of performing "Intensity Projection."

The parallax image generated from volume data by the three-dimensional image processing unit 1362 may be used as an underlay, and then an overlay image in which various types of information (e.g., scale, patient name, and test item) is represented may be superimposed thereon as an overlay.

In this case, the two-dimensional image processing unit 1363 performs image processing on an overlay image serving as an overlay and a parallax image serving as an underlay, thereby generating a parallax image having the overlay image superimposed. In the example illustrated in FIG. 5, the two-dimensional image processing unit 1363 includes a two-dimensional object drawing unit 1363*a*, a two-dimensional geometric transformation processing unit 1363*b*, and a luminance adjustment unit 1363*c*. In order to reduce the process cost of drawing various types of information, nine parallax images having an overlay image superimposed may be generated by drawing only one overlay and superimposing the one overlay on each of nine parallax images serving as underlays.

The two-dimensional object drawing unit 1363*a* draws various types of information to be represented in an overlay. The two-dimensional geometric transformation processing unit 1363*b* translates or rotates the position of various types of information to be represented in an overlay, or enlarges or reduces various types of information to be represented in an overlay. The luminance adjustment unit 1363*c* adjusts the luminance of the overlay and the underlay, for example, according to parameters for image processing, such as the gradation, the window width (WW), and the window level (WL) of a stereoscopic display monitor as an output destination. The luminance adjustment unit 1363*c* also performs, for example, a luminance conversion process on a rendering image.

The parallax image generated by the rendering processor 136 is, for example, temporarily stored in the storage unit 134 by the controller 135 and thereafter transmitted to the image storage device 120 through the communication unit 133. Thereafter, for example, the terminal device 140 acquires a parallax image having an overlay image superimposed from the image storage device 120, converts the acquired image into an intermediate image arranged in a prescribed format (for example, a grid pattern), and then displays the converted image on the stereoscopic display monitor, so that a stereoscopic image including various types of information (e.g., scale, patient name, and test item) represented can be displayed to doctors and laboratory technicians as users.

As described above, the rendering processor 136 generates a parallax image from volume data under the control of the controller 135. The controller 135 in the first embodiment will now be described in detail.

Figure 7:
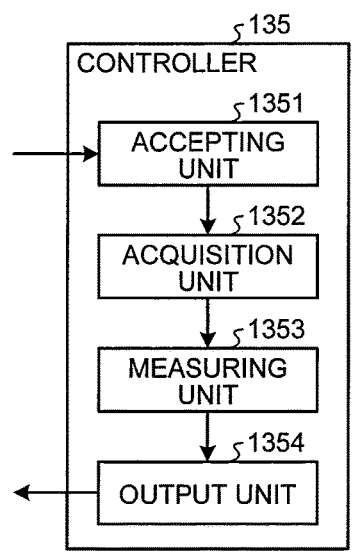
FIG. 7 is a diagram illustrating a controller in detail according to the first embodiment.

FIG. 7 is an example of a diagram for explaining the details of the controller in the first embodiment. As illustrated in FIG. 7, the controller 135 includes an accepting unit 1351, an acquisition unit 1352, a measuring unit 1353, and an output unit 1354.

The accepting unit 1351 accepts the setting of two coordinates in a stereoscopic image of a subject displayed on the stereoscopic display monitor of the terminal device 140 or the workstation 130. The terminal device 140 is also called a "stereoscopic image display device."

The accepting unit 1351 accepts the setting of a region of interest in a stereoscopic image of a subject displayed on the stereoscopic image display device. For example, the accepting unit 1351 accepts the setting of a partial region in any given cross section as the setting of a region of interest. For example, the accepting unit 1351 accepts the setting of any given region as the setting of a region of interest. In the case where the setting of any given region is accepted, the given region may be in spherical, cubic, rectangular, or any other shape. The setting of a region of interest is made by the user.

In other words, the region having any given shape as designated by the user serves as a region of interest.

For example, the accepting unit 1351 accepts, as the setting of a region of interest, the setting of any given axial plane or any given sagittal plane, any given coronal plane, or any given oblique cross section obtained by rotating the cross section with respect to the rotational axis designated by the user in a stereoscopic image of a subject. For example, the accepting unit 1351 accepts the setting of a three-dimensional region in any given shape.

The setting of a region of interest accepted by the accepting unit 1351 is made by any given method, for example, by the user who uses the workstation 130 or the terminal device 140. For example, the setting of a region of interest accepted by the accepting unit 1351 is made by the user using any pointing device such as a mouse.

Here, an example of a process of accepting the setting of coordinates or the setting of a region of interest will be described briefly. For example, when accepting an instruction from the user to start a process for accepting the setting of a region of interest, the accepting unit 1351 outputs to the rendering processor 136 the rendering conditions for generating a parallax image for displaying a stereoscopic image in which any given coordinates or any given region of interest is displayed, and allows the stereoscopic display monitor to display the parallax image generated by the rendering processor 136. That is, the accepting unit 1351 controls such that the stereoscopic display monitor displays a stereoscopic image in which any given coordinates are displayed or a stereoscopic image in which any given region is displayed as a region of interest. Then, when accepting an operation to change the position of the given coordinates or an operation to change the position or shape of the region of interest in the stereoscopic image, the accepting unit 1351 outputs to the rendering processor 136 the rendering conditions for generating a parallax image for displaying a stereoscopic image that reflects the contents of the accepted operation, and allows the stereoscopic display monitor to display the parallax image generated by the rendering processor 136. Thereafter, the accepting unit 1351 accepts an operation to determine from the user and then accepts the setting of coordinates or the setting of the region of interest at the time of accepting the operation. It is noted that the process of accepting the setting of a region of interest described above is illustrated by way of example only, and, without being limited thereto, the setting of a region of interest may be accepted by any method. In the description in the first embodiment, the accepting unit 1351 accepts the setting of two coordinates and the setting of a region of interest. However, embodiments are not limited thereto. For example, the accepting unit 1351 may accept the setting of two coordinates but may not accept the setting of a region of interest.

For example, when the setting of a region of interest is accepted, the accepting unit 1351 may accept one given coordinate and then accept a region of any given shape having the accepted coordinate at the center as a region of interest. For example, the accepting unit 1351 may accept any given coordinate and radius from the user to accept the setting of a sphere having the given coordinate at the center as a region of interest.

The acquisition unit 1352 acquires volume data coordinates that are coordinates in volume data of a subject stored in the image storage device 120, and that correspond to the stereoscopic image coordinates indicating the coordinates accepted by the accepting unit 1351. The image storage device 120 is also called a "prescribed storage device." The volume data coordinates serve as absolute coordinates with any given coordinates as a reference.

When the setting of a region of interest in a stereoscopic image of a subject displayed on the stereoscopic image display device is accepted by the accepting unit 1351, the acquisition unit 1352 acquires volume data coordinates corresponding to the stereoscopic image coordinates that are coordinates in the stereoscopic image for specifying the accepted region of interest. For example, the acquisition unit 1352 acquires volume data coordinates corresponding to the stereoscopic image coordinates indicating a partial region in any given cross section accepted by the accepting unit 1351. For example, the acquisition unit 1352 acquires volume data coordinates corresponding to the stereoscopic image coordinates for specifying any given three-dimensional region accepted by the accepting unit 1351. That is, for example, the acquisition unit 1352 acquires each volume data coordinate for use in measuring the area or volume of the region of interest accepted by the accepting unit 1351. To give a more detailed example, the acquisition unit 1352 acquires volume data coordinates for all the coordinates included in the region of interest or acquires volume data coordinates indicating the boundary between a region of interest and other region.

Here, the acquisition of volume data coordinates by the acquisition unit 1352 is additionally described. The scale, angle of view, and direction, for example, of the stereoscopic image displayed on the stereoscopic display monitor of the terminal device 140 or the workstation 130 can be optionally changed by the user. Of the scale of the stereoscopic image, the scale in the depth direction is not always equal to the actual scale because of the performance of the stereoscopic display monitor and may be smaller than the actual scale. As a result, even when a measuring process is executed using the coordinates in a stereoscopic image displayed on the terminal device 140, an exact value cannot be obtained. Based on this, the acquisition unit 1352 acquires volume data coordinates corresponding to stereoscopic image coordinates on purpose.

Stereoscopic image coordinates change every time the scale, parallax angle, and the like of a stereoscopic image is changed. Based on this, even when the scale, parallax angle, or the like of a stereoscopic image is changed, the acquisition unit 1352 acquires volume data coordinates corresponding to the stereoscopic image coordinates to allow the controller 135 to execute a measuring process using the volume data coordinates acquired before the change.

Examples of a method of measuring the distance between two points in a planar image include a conventional projection method in which two points are projected on a projection surface (display surface) and the distance between the two projected points is measured. In this respect, the conventional projection method, which does not consider the depth direction, cannot be applied to a stereoscopic image having a depth. Based on this, the controller 135 converts stereoscopic image coordinates into volume data coordinates and thereafter executes a measuring process based on the converted volume data coordinates.

Figure 8:
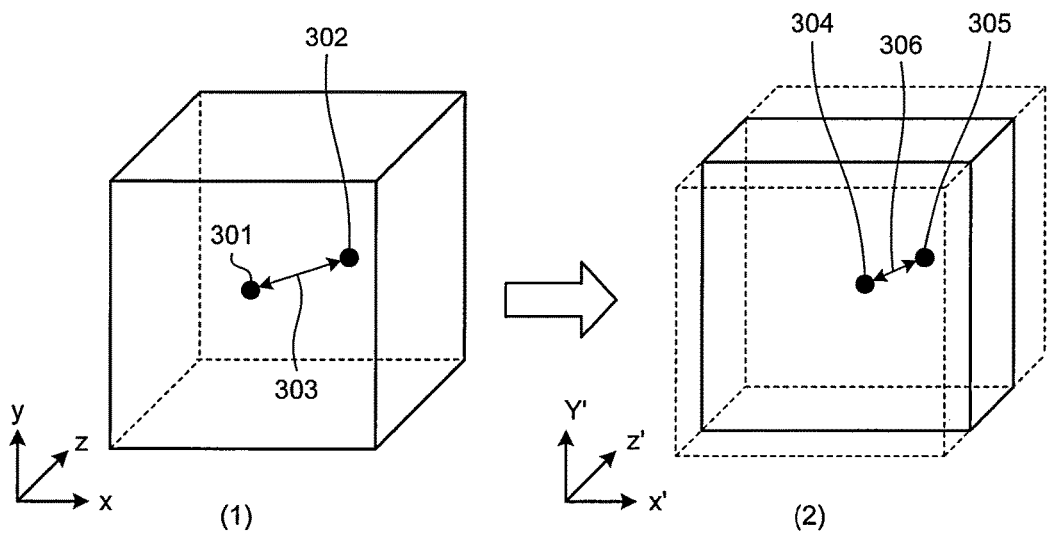
FIG. 8 is a diagram for explaining stereoscopic image coordinates and volume data coordinates according to the first embodiment.
Figure 9:
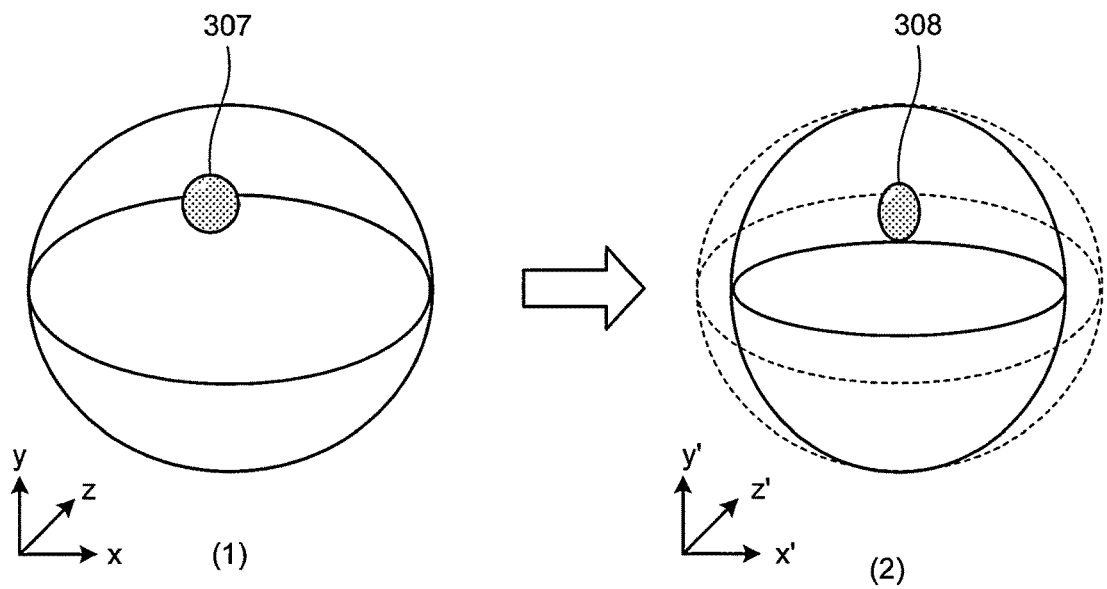
FIG. 9 is a diagram for explaining stereoscopic image coordinates and volume data coordinates according to the first embodiment.

FIG. 8 and FIG. 9 are diagrams for explaining stereoscopic image coordinates and volume data coordinates according to the first embodiment. In FIG. 8, (1) and (2) illustrate the same subject. In FIG. 9, (1) and (2) illustrate the same subject. In FIG. 8 and FIG. 9, (1) illustrates an example of a subject indicated by volume data coordinates in the first embodiment. For the sake of convenience of explanation, in the example illustrated in (1) in FIG. 8, the subject is represented with a cube, and in the example illustrated in (1) in FIG. 9, the subject is represented with a sphere. In FIG. 8 and FIG. 9, (2) illustrates an example of a stereoscopic image displayed on the terminal device 140. In FIG. 8 and FIG. 9, the z direction indicates the depth direction in real space coordinates, the x direction indicates the horizontal direction in real space coordinates, and the y direction indicates the vertical direction in real space coordinates. The z' direction indicates the depth direction in virtual space coordinates, the x' direction indicates the horizontal direction in virtual space coordinates, and the y' direction indicates the vertical direction in virtual space coordinates. A coordinate 301, a coordinate 302, and a distance 303 in (1) in FIG. 8 correspond to a coordinate 304, a coordinate 305, and a distance 306, respectively, in (2) in FIG. 8. A region of interest 307 in (1) in FIG. 9 corresponds to a region of interest 308 in (2) in FIG. 9.

When compared with the subject in the volume data illustrated in (1) in FIG. 8, the stereoscopic image in (2) in FIG. 8 is narrower in the depth direction. In other words, in the stereoscopic image in (2) in FIG. 8, the component in the depth direction of the subject illustrated in (1) in FIG. 8 is compressed to be displayed. In this case, as illustrated in (2) in FIG. 8, when compared with the distance 303 between the coordinate 301 and the coordinate 302 in (1) in FIG. 8, the distance 306 between the coordinate 304 and the coordinate 305 is shorter by the amount of compression of the distance in the depth direction. In other words, the distance 306 displayed in the stereoscopic image is shorter than the distance 303 in the real space.

When compared with the subject in the volume data illustrated in (1) in FIG. 9, the stereoscopic image in (2) in FIG. 9 is narrower in the z direction and the x direction. In other words, in the stereoscopic image in (2) in FIG. 9, the components in the depth direction and the horizontal direction of the subject illustrated in (1) in FIG. 9 are compressed to be displayed. In this case, as illustrated in (2) in FIG. 9, the shape of the region of interest 308 is narrower in the z direction and the x direction when compared with the "sphere" that is the shape of the region of interest 307 illustrated in (1) in FIG. 9. In the example illustrated in FIG. 9, the case of being narrower in the z direction and the x direction has been illustrated by way of example. However, embodiments are not limited thereto, and it is possible to be narrower only in the z direction or to be narrower in the y direction.

Here, a method of acquiring volume data coordinates corresponding to stereoscopic image coordinates by the acquisition unit 1352 will be described. The correspondence between stereoscopic image coordinates and volume data coordinates is uniquely determined based on the scale, angle of view, direction, and the like of a stereoscopic image, and can be expressed, for example, in the form as in Formula (1) below.

$$(x1, y1, z1) = F(x2, y2, z2) \qquad (1)$$

In Formula (1), "x2", "y2", and "z2" indicate stereoscopic image coordinates. "x1", "y1", and "z1" indicate volume data coordinates. "F" indicates a function. The function "F" is uniquely determined by the scale, angle of view, direction, and the like of a stereoscopic image. More specifically, in the example illustrated in Formula (1), the acquisition unit 1352 acquires volume data coordinates by processing the stereoscopic image coordinates of the accepted region of interest with the function "F." The function "F" is generated every time the scale, angle of view, direction, and the like of a stereoscopic image are changed. For example, affine transformation illustrated in Formula (2) is used as the function "F" for transforming rotation, translation, enlargement, or reduction.

$$x1=a*x2+b*y2+c*z3+d$$
$$y1=e*x2+f*y2+g*z3+h$$
$$z1=i*x2+j*y2+k*z3+1 \qquad (2)$$

(a to 1 are coefficients for transformation.)

In the foregoing description, the acquisition unit 1352 acquires volume data coordinates based on the function "F." However, embodiments are not limited thereto. For example, the image processing apparatus may have a coordinate table in which stereoscopic image coordinates are associated with volume data coordinates, and the acquisition unit 1352 may acquire volume data coordinates corresponding to stereoscopic image coordinates by searching the coordinate table using stereoscopic image coordinates as a search key.

The measuring unit 1353 executes a measuring process of measuring the distance between two coordinates accepted by the accepting unit 1351, based on the volume data coordinates acquired by the acquisition unit 1352.

When the setting of a region of interest in the stereoscopic image of a subject displayed on the stereoscopic image display device is accepted by the accepting unit 1351, the measuring unit 1353 execute a measuring process for the region of interest based on the volume data coordinates acquired by the acquisition unit 1352. Here, for example, the measuring unit 1353 may measure the total sum of CT values in the region of interest, may measure the mean value of CT values in the region of interest, may measure the maximum value of CT values or the minimum value of CT values in the region of interest, may measure the volume or area of the region of interest, or may execute any measuring process. The "CT value" described here is not limited to a CT value but may be substituted with any feature value.

The output unit 1354 outputs the result of measurement by the measuring unit 1353. For example, the output unit 1354 outputs the distance between coordinates or outputs the volume of the region of interest.

Process According to First Embodiment

Figure 10:
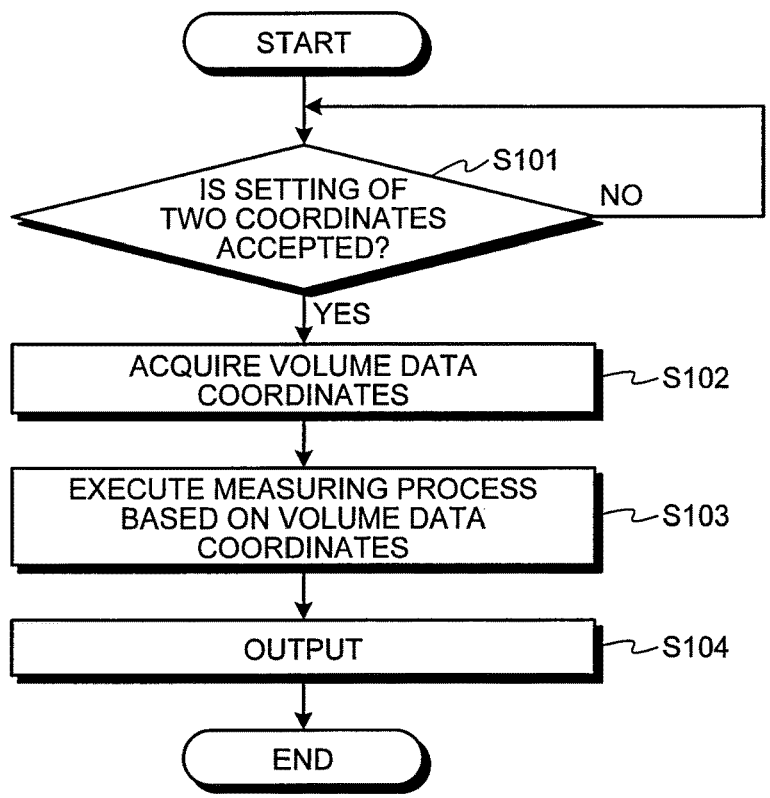
FIG. 10 is a flowchart illustrating an example of the flow of a process performed by the workstation according to the first embodiment.

Using FIG. 10, an example of a process flow in the workstation 130 according to the first embodiment will be described. FIG. 10 is a flowchart illustrating an example of the flow of a process performed by the image processing apparatus according to the first embodiment.

As illustrated in FIG. 10, in the workstation 130, when the setting of two coordinates in a stereoscopic image of a subject displayed on the stereoscopic display monitor of the terminal device 140 or the workstation 130 is accepted (Yes at step S101), the acquisition unit 1352 acquires volume data coordinates that are coordinates corresponding to stereoscopic image coordinates that are coordinates in a stereoscopic image indicating the accepted coordinates (step S102). For example, the acquisition unit 1352 acquires volume data coordinates by processing the accepted stereoscopic image coordinates of the region of interest with the function "F" based on Formula (1).

Then, the measuring unit 1353 executes a measuring process of measuring the distance between two coordinates accepted by the accepting unit 1351, based on the volume data coordinates acquired by the acquisition unit 1352 (step S103). For example, the measuring unit 1353 measures the distance between the coordinates accepted by the accepting unit 1351, based on the volume data coordinates acquired by the acquisition unit 1352.

Then, the output unit 1354 outputs the result of measurement by the measuring unit 1353 (step S104). For example, the output unit 1354 outputs the distance between coordinates.

Effects of First Embodiment

As described above, according to the first embodiment, the workstation 130 accepts the setting of two coordinates in a stereoscopic image of a subject displayed on the stereoscopic display monitor of the terminal device 140 or the workstation 130. The workstation 130 then acquires volume data coordinates that are coordinates corresponding to stereoscopic image coordinates indicating the accepted coordinates, and that are coordinates in volume data of the subjects that is stored in the image storage device 120. The workstation 130 then executes a measuring process of measuring the distance between the two coordinates based on the acquired volume data coordinates, and outputs the measurement result. As a result, a measuring process of measuring the distance between two coordinates set in a stereoscopic image can be executed accurately.

According to the first embodiment, the workstation 130 further accepts the setting of a region of interest in a stereoscopic image of a subject displayed on the stereoscopic display monitor of the terminal device 140 or the workstation 130. Then, the workstation 130 acquires volume data coordinates corresponding to stereoscopic image coordinates that are coordinates in the stereoscopic image included in the accepted region of interest. Then, the workstation 130 measures the volume or area of the region of interest accepted by the accepting unit, based on the acquired volume data coordinates. As a result, a measuring process of measuring the area or volume of a region of interest set in a stereoscopic image can be executed accurately.

Second Embodiment

Figure 11:
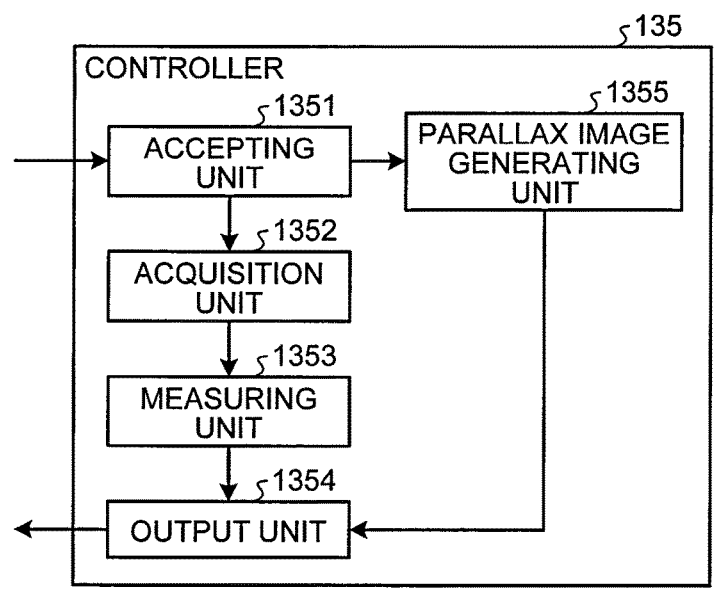
FIG. 11 is a diagram illustrating an exemplary configuration of a controller in a workstation according to a second embodiment.

FIG. 11 is a diagram illustrating an example of a configuration of the controller of the workstation according to a second embodiment. As illustrated in FIG. 11, the controller 135 further includes a parallax image generating unit 1355 that generates a parallax image for displaying a stereoscopic image, based on volume data stored in the image storage device 120. In the following, a description of the same points as in the first embodiment will be omitted. Although not being specifically mentioned, the controller 135 cooperates with the rendering processor 136 to generate a parallax image, in a similar manner as in the first embodiment.

Figure 12:
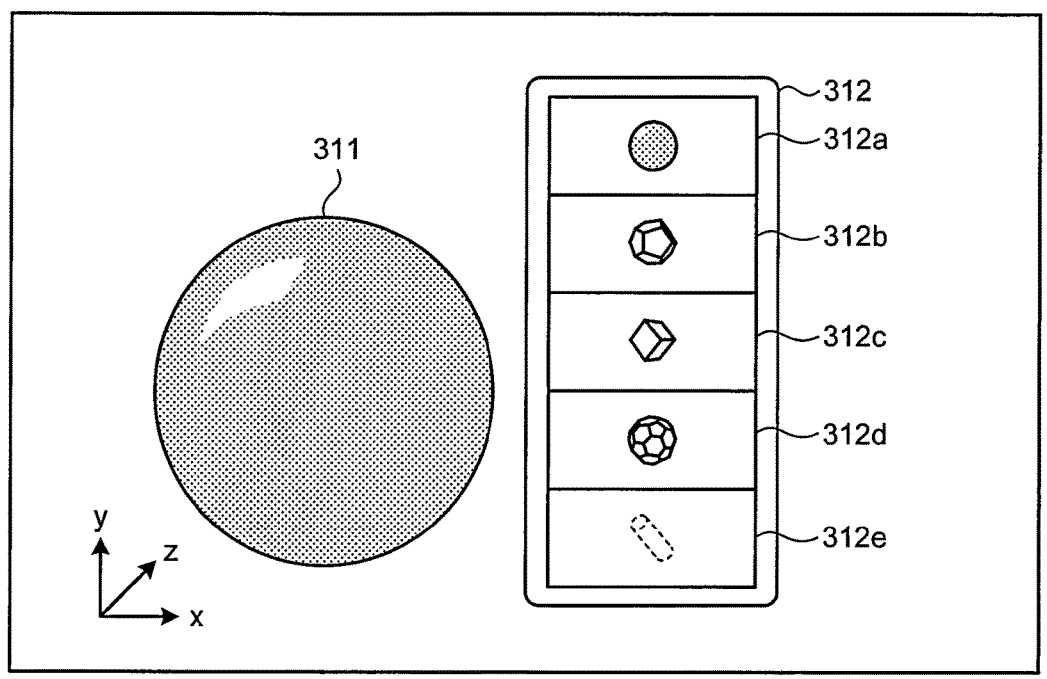
FIG. 12 is a diagram for explaining a parallax image generating unit according to the second embodiment.

The accepting unit 1351 in the second embodiment further accepts a display instruction to display an object of any given shape in a stereoscopic image. FIG. 12 is a diagram illustrating an example of the display instruction accepted by the accepting unit in the second embodiment. In the example illustrated in FIG. 12, the terminal device 140 displays a tool box 312 in addition to a stereoscopic image 311, by way of example. In the example illustrated in FIG. 12, the tool box 312 includes an icon 312a for accepting a display instruction to display a sphere, an icon 312b for accepting a display instruction to display a regular hexahedron, an icon 312c for accepting a display instruction to display a cube, an icon 312d for accepting a display instruction to display a regular dodecahedron, and an icon 312e for accepting a display instruction to display a straight line. Here, in the example illustrated in FIG. 12, when the user selects the icon 312a at the terminal device 140, the accepting unit 1351 accepts a display instruction to display a sphere.

The setting of a region of interest by the user may be accepted using each graphic in FIG. 12. In this case, the shape of each graphic in FIG. 12 may be optionally changed. For example, the region set as a region of interest may be enlarged by zooming each graphic in FIG. 12. A free region of any given shape may be set as a region of interest. The case where any given shape is set as a region of interest will be described. For example, as the initial setting, a stereoscopic image having any given shape is displayed to the user. In the following description, for the sake of convenience of explanation, a stereoscopic image having a sphere is displayed to the user as the initial setting. Thereafter, the shape of the graphic is deformed at the user's choice by accepting an operation of selecting part of the sphere from the user, and accepting an operation of deforming the sphere by pushing the selected portion toward the inside of the sphere, or an operation of deforming the sphere by drawing the selected portion toward the outside of the sphere. The selected portion may be in pointed, circular, quadrature, or any other shapes.

The parallax image generating unit 1355 changes the given shape indicated by the display instruction accepted by the accepting unit 1351 based on the scale of the stereoscopic image, and generates a parallax image for displaying a stereoscopic image that includes the object having the given shape changed, based on the volume data stored in the image storage device 120. The parallax image generating unit 1355 is also called a "first parallax image generating unit."

Figure 13:
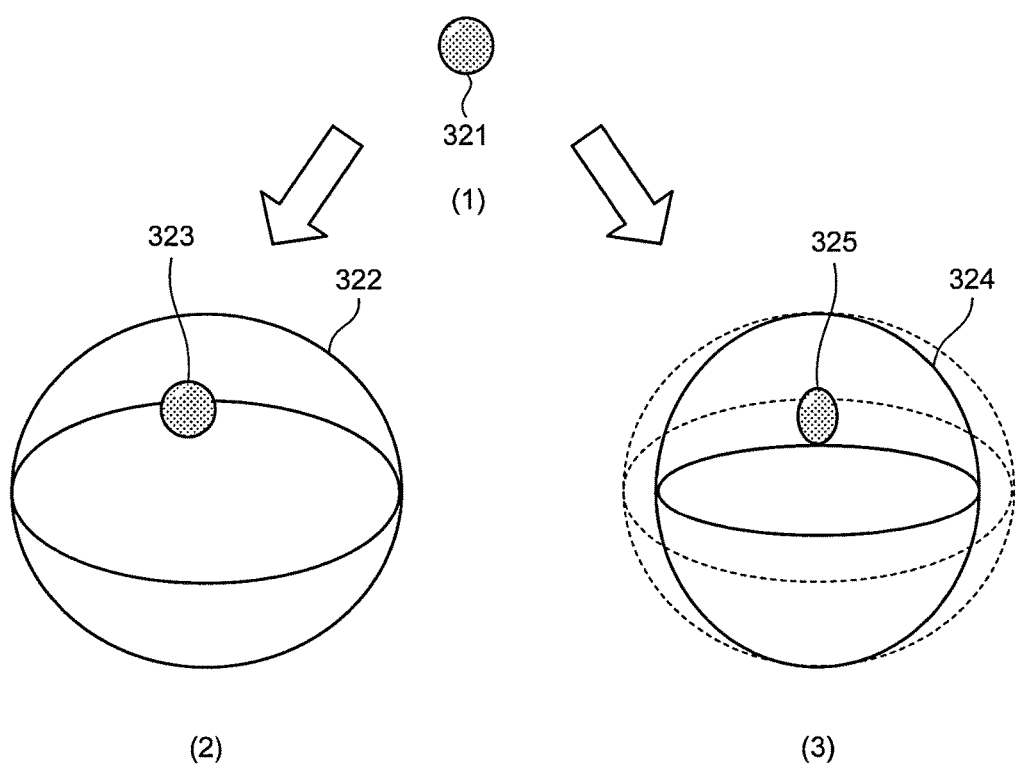
FIG. 13 is a diagram for explaining the parallax image generating unit according to the second embodiment.

FIG. 13 is a diagram for explaining the parallax image generating unit according to the second embodiment. As illustrated in (1) in FIG. 13, a description will be given using a case where the accepting unit 1351 accepts a display instruction to display a spherical object 321. Using (2) in FIG. 13, a case where the shape of a subject indicated by volume data coordinates is the same as the shape of a stereoscopic image 322 displayed on the stereoscopic display monitor will be described. In other words, the stereoscopic display monitor of the terminal device 140 or the workstation 130 displays parallax images for displaying a stereoscopic image having the same scale as the subject indicated by volume data coordinates. In this case, the parallax image generating unit 1355 generates parallax images for displaying a stereoscopic image that includes the spherical object 321 as it is without changing the scale and the like of the spherical object 321. In FIG. 13, (2) illustrates an example of the stereoscopic image displayed with the parallax images generated by the parallax image generating unit 1355. The shape of an object 323 in (2) in FIG. 13 is the same as the shape of the object 321.

Using (3) in FIG. 13, a case where the shape of the subject illustrated by volume data coordinates is not the same as the shape of a stereoscopic image 324 displayed on the stereoscopic display monitor will be described. In other words, the terminal device 140 displays a stereoscopic image on a scale different from that of the subject indicated by volume data coordinates. In this case, the parallax image generating unit 1355 changes the scale of the spherical object 321 and then generates a parallax image for displaying a stereoscopic image that includes the spherical object 321 with the scale changed. For example, in the example illustrated in (3) in FIG. 13, a parallax image for displaying a stereoscopic image that includes an object compressed in the x direction and the z direction of the sphere is generated. In FIG. 13, (3) illustrates an example of a stereoscopic image displayed with the parallax image generated by the parallax image generating unit 1355. The shape of an object 325 in (3) in FIG. 13 is not the same as the object 321. More specifically, when the scale, angle of view, direction, or the like of a stereoscopic image is changed when compared with the subject indicated by volume data coordinates, the parallax image generating unit 1355 reflects the changed scale, angle of view, direction, or the like on the object in the given shape. In other words, the parallax image generating unit 1355 changes the shape of the object displayed in the stereoscopic image in accordance with the scale, angle of view, and direction of the stereoscopic image.

The output unit 1354 outputs the parallax image generated by the parallax image generating unit 1355 to the terminal device 140. The output unit 1354 is also called a "first parallax image output unit."

Process According to Second Embodiment

Using FIG. 14, an example of the flow of a process performed by the image processing apparatus according to the second embodiment will be described. FIG. 14 is a flowchart illustrating an example of the flow of a process performed by the workstation 130 according to the second embodiment.

As illustrated in FIG. 14, in the workstation 130, when a display instruction is accepted (Yes at step S201), the parallax image generating unit 1355 changes the given shape indicated by the display instruction based on the scale of the stereoscopic image (step S202) and generates a parallax image for displaying a stereoscopic image that includes an object having the given shape changed, based on the volume data stored in the image storage device 120 (step S203). For example, the parallax image generating unit 1355 generates a parallax image for displaying a stereoscopic image that includes an object compressed in the x direction and the z direction of a sphere.

Then, the output unit 1354 outputs the parallax image generated by the parallax image generating unit 1355 to the terminal device 140 (step S204).

Effects of Second Embodiment

As described above, according to the second embodiment, a display instruction to display an object of any given shape in a stereoscopic image is further accepted. The parallax image generating unit 1355 changes the given shape indicated by the accepted display instruction, based on the scale of the stereoscopic image, and generates a parallax image for displaying a stereoscopic image that includes an object having the given shape changed, based on the volume data stored in the image storage device 120. Then, according to the second embodiment, the generated parallax image is output to the stereoscopic image display device. As a result, the user can easily understand the change in scale, angle of view, or direction in the stereoscopic image.

Third Embodiment

An embodiment other than the foregoing embodiments may be carried out. Then, another embodiment will be illustrated below.

Connecting Operation

For example, the accepting unit 1351 may accept a connecting operation of connecting ends of two line segments displayed in a stereoscopic image. In this case, to set a region of interest, the workstation 130 accepts a connecting operation of connecting ends of two line segments displayed in a stereoscopic image, acquires volume data coordinates corresponding to stereoscopic image coordinates indicating the two line segments connected by the connecting operation, and measures the angle between the two line segments based on the acquired volume data coordinates. As a result, the angle between the two line segments can be measured accurately.

Figure 15A:
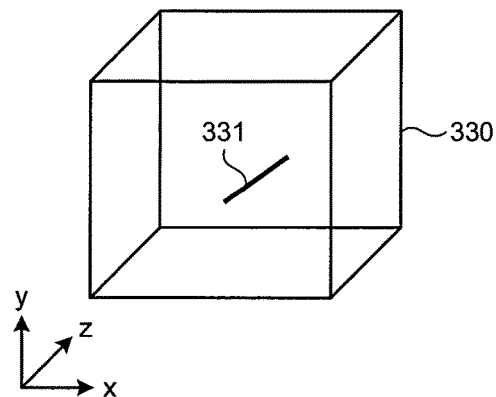
FIG. 15A is a diagram illustrating an example of a connecting operation.
Figure 15B:
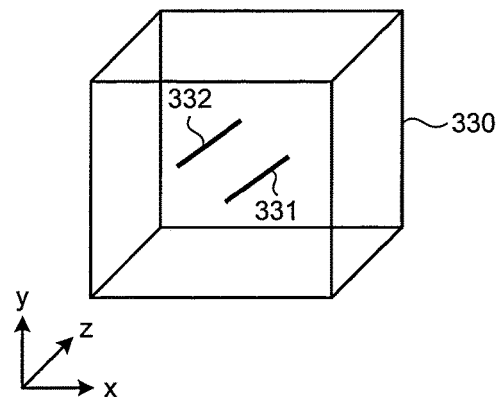
FIG. 15B is a diagram illustrating an example of the connecting operation.
Figure 15C:
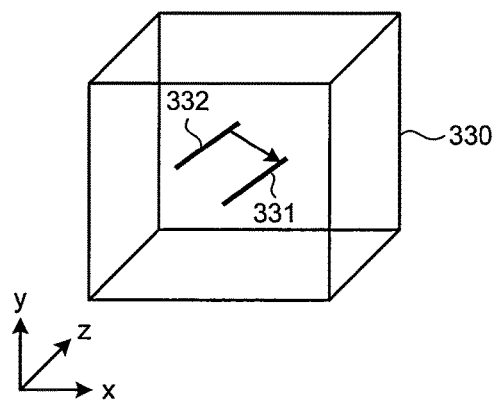
FIG. 15C is a diagram illustrating an example of the connecting operation.
Figure 15D:
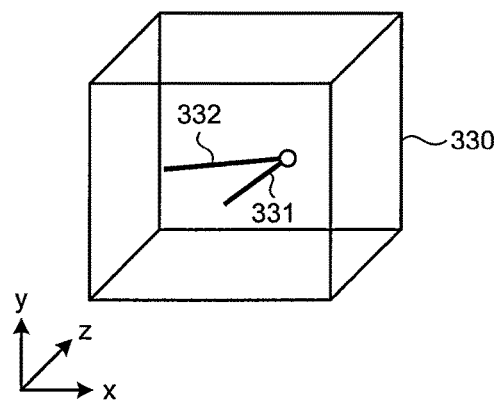
FIG. 15D is a diagram illustrating an example of the connecting operation.

In the controller 135 of the image processing apparatus, a case where the accepting unit 1351 further accepts a connecting operation of connecting ends of two line segments displayed in a stereoscopic image will be further described. FIG. 15A to FIG. 15D are diagrams illustrating an example of the connecting operation. As illustrated in FIG. 15A, when the accepting unit 1351 accepts a display operation to display a first straight line, the parallax image generating unit 1355 generates a parallax image for displaying a stereoscopic image 330 including a straight line 331. Then, as illustrated in FIG. 15B, when the accepting unit 1351 accepts a display operation to display a second straight line, the parallax image generating unit 1355 generates a parallax image for displaying the stereoscopic image 330 including a straight line 332. Then, when the accepting unit 1351 accepts an operation to bring the end of the straight line 332 closer to the straight line 331 as illustrated in FIG. 15C, the parallax image generating unit 1355 generates a parallax image for displaying the stereoscopic image 330 in which the end of the straight line 332 is connected to the straight line 331 as illustrated in FIG. 15D.

Thereafter, the acquisition unit 1352 acquires volume data coordinates corresponding to the stereoscopic image coordinates indicating the two line segments accepted by the accepting unit 1351, and the measuring unit 1353 measures the angle between the two line segments based on the volume data coordinates acquired by the acquisition unit 1352. As a result, the user can easily measure the angle between two line segments.

Changing Operation on Stereoscopic Image

For example, the accepting unit 1351 may further accept a changing operation of changing at least one of the angle of view, scale, and direction of a stereoscopic image displayed on the stereoscopic image display device. In this case, the parallax image generating unit 1355 generates a parallax image for displaying a stereoscopic image that reflects the change through the changing operation accepted by the accepting unit 1351, based on the volume data of the subject that is stored in the image storage device 120, and the output unit 1354 outputs the parallax image generated by the parallax image generating unit 1355 to the terminal device 140. The parallax image generating unit 1355 is also called a "second parallax image generating unit," and the output unit 1354 is also called a "second parallax image output unit." As a result, a region of interest can be easily set by optionally changing the angle of view, scale, or direction.

Distance Measurement

Figure 16:
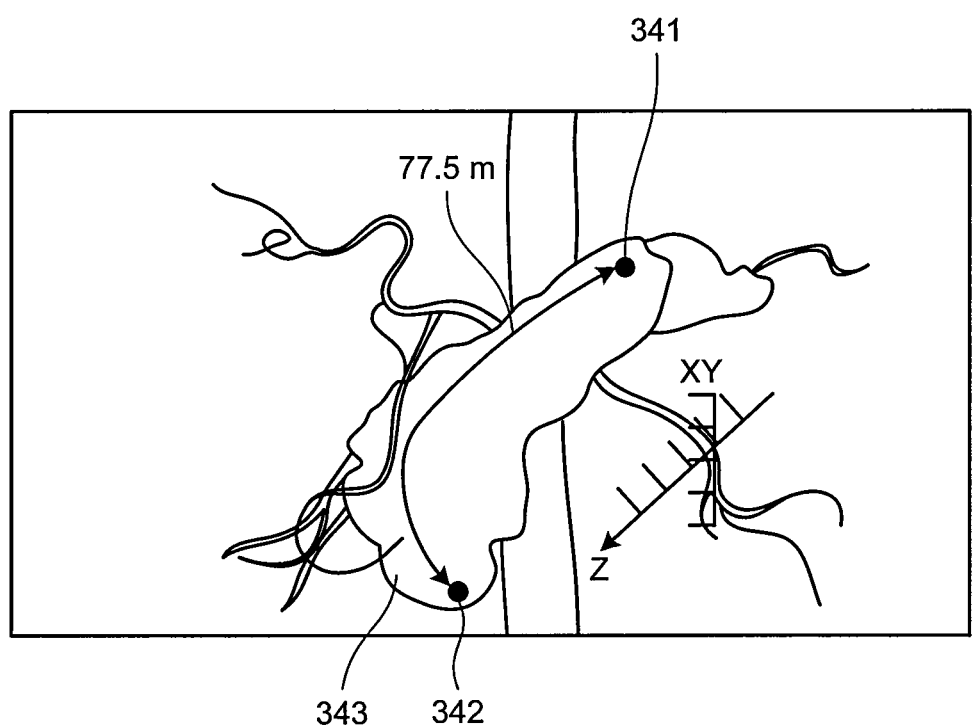
FIG. 16 is a diagram illustrating an example of a distance measured by a measuring unit.

For example, to measure a distance, the measuring unit 1353 may measure the distance along the surface of an organ or blood vessel rather than measuring the distance that connects coordinates with a straight line. FIG. 16 is a diagram illustrating an example of the distance measured by the measuring unit. In the example illustrated in FIG. 16, the measuring unit 1353 may measure the distance along the surface of an organ 343, rather than measuring the distance that connects a coordinate 341 and a coordinate 342 with a straight line. In this case, the measuring unit 1353 may determine whether the two coordinates are present on the same organ or blood vessel, and when determining that they are, may measure the distance along the organ or blood vessel. When the user designates an organ or blood vessel, the measuring unit 1353 may measure the distance along the surface of the designated blood vessel or organ.

Content of Measurement

For example, the measuring unit 1353 may output volume data coordinates per se as a measurement result.

Shape of Graphic

For example, when any given shape is displayed on a stereoscopic image, the designated shape may be displayed as it is on a stereoscopic image. For example, when a sphere is selected, a stereoscopic image having a sphere may be displayed to the user. A case where the shape on volume data corresponding to a sphere on a stereoscopic image is an oval sphere will be further described. In this case, when the user selects a sphere, the workstation 130 may display to the user a stereoscopic image having a sphere that is the designated shape. In other words, a stereoscopic image having a graphic that is a sphere on a stereoscopic image and is an oval sphere on volume data may be displayed to the user.

Setting of Region of Interest

For example, when the setting of a region of interest is accepted with the shape of the region of interest changed, the parallax image generating unit 1355 may generate and output a parallax image for displaying a stereoscopic image in which the changed region of interest is displayed. Here, in a case where the shape of a region of interest is spherical, the controller may be moved with the terminal device 140 in depth or upward, downward, leftward, or rightward with a viewpoint at the center of depth coordinates, ordinates, and abscissas whereby the accepting unit 1351 may accept designation of the diameter, or the border of the sphere may be dragged again with the terminal device 140 whereby the accepting unit 1351 may accept a change in the diameter.

For example, when the shape of a region of interest is rectangular, the accepting unit 1351 may accept an instruction to superimpose a rectangle. When the shape of a region of interest is spherical, the region of interest can be designated efficiently by deforming the shape freely so as to include the region of interest into a sphere.

In the foregoing description of embodiments, the workstation 130 generates parallax images based on volume data. However, embodiments are not limited thereto. For example, the medical image diagnosis device 110 or the terminal device 140 may generate parallax images based on volume data. In this case, the medical image diagnosis device 110 or the terminal device 140 has a function corresponding to the controller 135 and the rendering processor 136. For example, one or more of the workstation 130, the medical image diagnosis device 110, and the terminal device 140 may corporate to generate parallax images based on volume data.

In the foregoing description of embodiments, the workstation 130 acquires volume data from the image storage device 120. However, embodiments are not limited thereto. For example, the workstation 130 may acquire volume data from the medical image diagnosis device 110.

Content Accepted by Accepting Unit

In the foregoing description of embodiments, the accepting unit 1351 accepts the setting of two coordinates, accepts the setting of a region of interest, and accepts a connecting operation. Here, the accepting unit 1351 may accept any setting or operation, among the setting of two coordinates, the setting of a region of interest, and the connecting operation. For example, the accepting unit 1351 may accept only the setting of a region of interest, may accept only the connecting operation, or may accept only the setting of two coordinates.

(System Configuration)

Among the processes described in the foregoing embodiments, the process that has been described as being performed automatically may be entirely or partially performed manually, or the process that has been described as being performed manually may be entirely or partially performed automatically by a known method. In addition, the process procedures, control procedures, specific names, and information including a variety of data and parameters illustrated in the foregoing description and the drawings (FIG. 1 to FIG. 16) may be optionally changed, unless otherwise specified.

The components in each illustrated device are functional and conceptual and are not necessarily physically configured as illustrated in the drawings. Specifically, the specific embodiment of distribution and integration of the devices is not limited to that illustrated in the drawings, and the entire or part of the components may be configured to be functionally or physically distributed or integrated in any unit depending on load and use conditions. For example, the controller 135 of the workstation 130 may be connected as a device external to the workstation 130 via a network.

Others

A computer program for executing the image processing program system described in the present embodiment can be distributed over a network such as the Internet. The image processing program may be stored in a computer-readable recording medium such as a hard disk, a flexible disk (FD), a compact disk read only memory (CD-ROM), a magneto-optical disk (MO), a digital versatile disk (DVD), or a Blu-ray (registered trademark) Disc and may be read by a computer from the recording medium for execution.

Effects of Embodiments

In the image processing apparatus according to at least one of the foregoing embodiments, the setting of a region of interest in a stereoscopic image of a subject displayed on a stereoscopic image display device is accepted, a planar image corresponding to the accepted region of interest is generated based on volume data, and the generated planar image is output, whereby the positional relationship in the stereoscopic image can be grasped.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system, comprising:
processing circuitry configured to:
generate a first plurality of parallax images for displaying a stereoscopic image virtually observed in three-dimensional virtual space coordinates, and output the first plurality of parallax images, wherein the stereoscopic image includes a subject and two points;
accept a movement operation for moving positions of the two points on the stereoscopic image;
generate a second plurality of parallax images for displaying the stereoscopic image in which the two points are displayed at positions after a movement in accordance with acceptance of the movement operation, and output the second plurality of parallax images;
accept setting of two coordinates on the stereoscopic image, by accepting an operation to determine positions of the two points on the stereoscopic image;
acquire two coordinates in real space coordinates corresponding to the two coordinates in the three-dimensional virtual space coordinates by converting stereoscopic image coordinates for indicating the two coordinates accepted on the stereoscopic image into volume data coordinates corresponding to the stereoscopic image coordinates in volume data of the subject that is stored in a prescribed storage circuitry;
execute a measuring process of measuring a distance between the two coordinates in the real space coordinates; and
output a result of measurement.

2. The image processing system according to claim 1, wherein the processing circuitry is further configured to:
accept a connecting operation of connecting ends of two line segments in the three-dimensional virtual space coordinates by accepting the connecting operation of connecting ends of the two line segments displayed in the stereoscopic image;
acquire coordinates indicating the two line segments in the real space coordinates by converting the stereoscopic image coordinates indicating the two line segments connected through the connecting operation into volume data coordinates corresponding to the stereoscopic image coordinates; and
execute a measuring process of measuring an angle between the two line segments in the real space coordinates based on the volume data coordinates.

3. The image processing system according to claim 1, wherein the processing circuitry is further configured to:
accept a changing operation of changing at least one of the angle of view, the scale, and the direction of the stereoscopic image displayed on the stereoscopic image display;
generate a parallax image for the stereoscopic image that reflects a change made by the changing operation accepted, based on the volume data of the subject that is stored in the prescribed storage circuitry; and
output the parallax image generated to the stereoscopic image display.

4. An image processing method, comprising:
generating a first plurality of parallax images for displaying a stereoscopic image virtually observed in three-dimensional virtual space coordinates, and outputting the first plurality of parallax images, wherein the stereoscopic image includes a subject and two points;
accepting a movement operation for moving positions of the two points on the stereoscopic image;
generating a second plurality of parallax images for displaying the stereoscopic image in which the two points are displayed at positions after a movement in accordance with acceptance of the movement operation, and outputting the second plurality of parallax images;
accepting setting of two coordinates on the stereoscopic image, by accepting an operation to determine positions of the two points on the stereoscopic image;
acquiring two coordinates in real space coordinates corresponding to the two coordinates in the three-dimensional virtual space coordinates by converting stereoscopic image coordinates for indicating the two coordinates accepted on the stereoscopic image into volume data coordinates corresponding to the stereoscopic image coordinates in volume data of the subject that is stored in a prescribed storage;

executing a measuring process of measuring a distance between the two coordinates in the real space coordinates; and outputting a result of measurement.

5. An image processing apparatus, comprising:
processing circuitry configured to:
generate a first plurality of parallax images for displaying a stereoscopic image virtually observed in three-dimensional virtual space coordinates, and output the first plurality of parallax images, wherein the stereoscopic image includes a subject and two points;
accept a movement operation for moving positions of the two points on the stereoscopic image;
generate a second plurality of parallax images for displaying the stereoscopic image in which the two points are displayed at positions after a movement in accordance with acceptance of the movement operation, and output the second plurality of parallax images;
accept setting of two coordinates on the stereoscopic image, by accepting an operation to determine positions of the two points on the stereoscopic image;
acquire two coordinates in real space coordinates corresponding to the two coordinates in the three-dimensional virtual space coordinates by converting stereoscopic image coordinates for indicating the two coordinates accepted on the stereoscopic image into volume data coordinates corresponding to the stereoscopic image coordinates in volume data of the subject that is stored in a prescribed storage circuitry;
execute a measuring process of measuring a distance between the two coordinates in the real space coordinates; and
output a result of measurement.

6. An image processing system, comprising:
processing circuitry configured to:
generate a first plurality of parallax images for displaying a stereoscopic image virtually observed in three-dimensional virtual space coordinates, and output the first plurality of parallax images, wherein the stereoscopic image includes a subject and any given region;
accept a change operation for changing at least one of position and shape of the given region on the stereoscopic image;
generate a second plurality of parallax images for displaying the stereoscopic image in which the given region is displayed in a position and shape after a change in accordance with acceptance of the change operation, and output the second plurality of parallax images;
accept setting of a region of interest on the stereoscopic image, by accepting an operation to determine a position and shape of the given region on the stereoscopic image;
acquire region of interest in real space coordinates corresponding to the region of interest in the three-dimensional virtual space coordinates by converting stereoscopic image coordinates for indicating the region of interest accepted on the stereoscopic image into volume data coordinates corresponding to the stereoscopic image coordinates in volume data of the subject that is stored in a prescribed storage circuitry;
execute a measuring process for the region of interest in the real space coordinates, by using the volume data coordinates; and
output a result of measurement.

7. The image processing system according to claim 6, wherein the processing circuitry is further configured to:
accept a connecting operation of connecting ends of two line segments in the three-dimensional virtual space coordinates by accepting the connecting operation of connecting ends of the two line segments displayed in the stereoscopic image;
acquire coordinates indicating the two line segments in the real space coordinates by converting the stereoscopic image coordinates indicating the two line segments connected through the connecting operation into volume data coordinates corresponding to the stereoscopic image coordinates; and
execute a measuring process of measuring an angle between the two line segments in the real space coordinates based on the volume data coordinates.

8. The image processing system according to claim 6, wherein the processing circuitry is further configured to:
accept a changing operation of changing at least one of the angle of view, the scale, and the direction of the stereoscopic image displayed on the stereoscopic image display;
generate a parallax image for the stereoscopic image that reflects a change made by the changing operation accepted, based on the volume data of the subject that is stored in the prescribed storage circuitry; and
output the parallax image generated to the stereoscopic image display.

9. An image processing method, comprising:
generating a first plurality of parallax images for displaying a stereoscopic image virtually observed in three-dimensional virtual space coordinates, and outputting the first plurality of parallax images, wherein the stereoscopic image includes a subject and any given region;
accepting a change operation for changing at least one of position and shape of the given region on the stereoscopic image;
generating a second plurality of parallax images for displaying the stereoscopic image in which the given region is displayed in position and shape after a change in accordance with acceptance of the change operation, and outputting the second plurality of parallax images;
accepting setting of a region of interest on the stereoscopic image, by accepting an operation to determine a position and shape of the given region on the stereoscopic image;
acquiring a region of interest in real space coordinates corresponding to the region of interest in the three-dimensional virtual space coordinates by converting stereoscopic image coordinates for indicating the region of interest accepted on the stereoscopic image into volume data coordinates corresponding to the stereoscopic image coordinates in volume data of the subject that is stored in a prescribed storage circuitry;
executing a measuring process for the region of interest in the real space coordinates, by using the volume data coordinates; and
outputting a result of measurement.

10. An image processing apparatus, comprising:
processing circuitry configured to:
generate a first plurality of parallax images for displaying a stereoscopic image virtually observed in three-dimensional virtual space coordinates, and output the first plurality of parallax images, wherein the stereoscopic image includes a subject and any given region;

accept a change operation for changing at least one of position and shape of the given region on the stereoscopic image;

generate a second plurality of parallax images for displaying the stereoscopic image in which the given region is displayed in position and shape after a change in accordance with acceptance of the change operation, and output the second plurality of parallax images;

accept setting of a region of interest on the stereoscopic image, by accepting an operation to determine a position and shape of the given region on the stereoscopic image;

acquire region of interest in real space coordinates corresponding to the region of interest in the three-dimensional virtual space coordinates by converting stereoscopic image coordinates for indicating the region of interest accepted on the stereoscopic image into volume data coordinates corresponding to the stereoscopic image coordinates in volume data of the subject that is stored in a prescribed storage circuitry;

execute a measuring process for the region of interest in the real space coordinates, by using the volume data coordinates; and output a result of measurement.

* * * * *